United States Patent
Powers

(10) Patent No.: US 6,235,929 B1
(45) Date of Patent: *May 22, 2001

(54) TRIPEPTIDE α-KETOAMIDES

(75) Inventor: James C Powers, Atlanta, GA (US)

(73) Assignee: Georgia Tech Research Corporation, Atlanta, GA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/777,354

(22) Filed: Dec. 27, 1996

Related U.S. Application Data

(63) Continuation-in-part of application No. 08/539,944, filed on Oct. 6, 1995, now Pat. No. 5,650,508, which is a continuation of application No. 08/246,511, filed on May 20, 1994, now abandoned, which is a continuation of application No. 08/118,997, filed on Sep. 9, 1993, now abandoned, which is a continuation of application No. 07/815,073, filed on Dec. 27, 1991, now abandoned.

(51) Int. Cl.$^7$ ................................................. C07L 229/00
(52) U.S. Cl. .......................... 562/450; 544/168; 548/334; 548/496; 548/535; 560/24; 560/32; 560/38; 560/40; 560/41; 560/45; 560/125; 560/159; 560/169; 562/449; 562/561; 564/153; 564/157; 564/159
(58) Field of Search ................................. 560/32, 38, 40, 560/41, 45, 125, 159, 169, 24; 548/334, 496, 535; 544/168; 564/153, 157, 159; 562/450, 449, 561

(56) References Cited

U.S. PATENT DOCUMENTS

| | | | | |
|---|---|---|---|---|
| 5,371,072 | * | 12/1994 | Webb | 514/18 |
| 5,444,042 | * | 8/1995 | Bartas | 514/2 |
| 5,496,927 | * | 3/1996 | Kolb | 530/328 |
| 5,514,694 | * | 5/1996 | Powers | 514/357 |
| 5,541,290 | * | 7/1996 | Harbeson | 530/330 |
| 5,597,804 | * | 1/1997 | Webb | 514/18 |
| 5,610,297 | * | 3/1997 | Powers | 544/168 |

FOREIGN PATENT DOCUMENTS

| | | |
|---|---|---|
| 195212 | 9/1986 | (EP). |
| 363284 | 4/1990 | (EP). |
| 92/12140 | * 7/1992 | (WO). |

OTHER PUBLICATIONS

Hu, Arch. Biochem. Biophys., 281, pp. 271–274 (received from PTO Sep. 10, 1990).

Burkhart, Tetrahedron Lett., 29, pp. 3433–3436 (1988).

Angelastro, et al., Journal of Medicinal Chemistry, 33, pp. 11–13 (1990).

Zhaozhao, et al., Journal of Medicinal Chemistry, 36, pp. 3472–3480 (1993).

* cited by examiner

Primary Examiner—Michael L. Shippen
(74) Attorney, Agent, or Firm—Todd Deveau; Ryan A. Schneider; Troutman Sanders LLP

(57) ABSTRACT

A novel class of tripeptide α-ketoamides useful for selectively inhibiting serine proteases, selectively inhibiting cysteine proteases, generally inhibiting all serine proteases, and generally inhibiting all cysteine proteases, having the formula $$M_1—AA—AA—AA—CO—NR_3R_4.$$

6 Claims, No Drawings

TRIPEPTIDE α-KETOAMIDES

This is a continuation-in-part of application(s) Ser. No. 08/539,944 filed on Oct. 6, 1995, now U.S. Pat. No. 5,650, 508 which is a continuation of Ser. No. 8/246,511, filed on May 20, 1994, now abandoned; which is a continuation of Ser. No. 08/118,997, filed Sep. 9, 1993, now abandoned; which is a continuation of Ser. No. 07/815,073, filed Dec. 27, 1991, now abandoned.

BACKGROUND OF THE INVENTION

1. Field of the Invention

This invention relates to a novel class of peptide ketoamides useful for selectively inhibiting serine proteases, selectively inhibiting cysteine proteases, generally inhibiting all serine proteases, and generally inhibiting all cysteine proteases. Serine proteases and cysteine proteases are involved in numerous disease states and inhibitors for these enzymes can be used therapeutically for the treatment of diseases involving serine proteases or cysteine proteases. We have discovered that peptide α-ketoamides can be constructed to inhibit selectively individual serine or cysteine proteases or groups of serine or cysteine proteases. We have found that peptide ketoamides which contain hydrophobic aromatic amino acid residues in the $P_1$ site are potent inhibitors of chymases and chymotrypsin-like enzymes. Ketoamides containing small hydrophobic amino acid residues at the $P_1$ position are good inhibitors of elastases. Inhibitors of elastases and chymases are useful as anti-inflammatory agents. We show that peptide ketoamides which contain cationic amino acid residues such as Arg and Lys in the $P_1$ site will be potent inhibitors of trypsin and blood coagulation enzymes. These inhibitors are thus useful as anticoagulants. Cysteine proteases such as papain, cathepsin B, and calpain I and II are also inhibited by ketoamides. Ketoamides with aromatic amino acid residues in the $P_1$ site are good inhibitors for cathepsin B and papain. Thus, they would have utility as anticancer agents. Ketoamides with either aromatic amino acid residues or small hydrophobic alkyl amino acid residues at $P_1$ are good inhibitors of calpain I and II. These inhibitors are useful as neuroprotectants and can be used as therapeutics for the treatment of neurodegeneration and stroke.

2. Nomenclature

In discussing the interactions of peptides with serine and cysteine proteases, we have utilized the nomenclature of Schechter and Berger [*Biochem. Biophys. Res. Commun.* 27, 157–162 (1967); incorporated herein by reference]. The individual amino acid residues of a substrate or inhibitor are designated $P_1$, $P_2$, etc. and the corresponding subsites of the enzyme are designated $S_1$, $S_2$, etc. The scissile bond of the substrate is $S_1$–$S_1'$. The primary substrate recognition site of serine proteases is $S_1$. The most important recognition subsites of cysteine proteases are $S_1$ and $S_2$.

Amino acid residues and blocking groups are designated using standard abbreviations [see J. Biol. Chem. 260, 14–42 (1985) for nomenclature rules; incorporated herein by reference]. An amino acid residue (AA) in a peptide or inhibitor structure refers to the part structure —NH—CHR$_1$—CO—, where R$_1$ is the side chain of the amino acid residue AA. A peptide α-ketoester residue would be designated —AA—CO—OR which represents the part structure —NH—CHR$_1$—CO—CO—OR. Thus, the ethyl ketoester derived from benzoyl alanine would be designated Bz—Ala—CO—OEt which represents $C_6H_5CO$—NH—CHMe—CO—CO—OEt. Peptide ketoamide residues would be designated —AA—CO—NH—R. Thus, the ethyl keto amide derived from Z—Leu—Phe—OH would be designated Z—Leu—Phe—CO—NH—Et which represents $C_6H_5CH_2OCO$—NH—CH($CH_2CHMe_2$)—CO—NH—CH($CH_2Ph$)—CO—CO—NH—Et.

3. Description of the Related Art

Cysteine Proteases

Cysteine proteases such as calpain use a cysteine residue in their catalytic mechanism in contrast to serine proteases which utilize a serine residue. Cysteine proteases include papain, cathepsin B, calpains, and several viral enzymes. Neural tissues, including brain, are known to possess a large variety of proteases, including at least two calcium stimulated proteases termed calpains. Calpains are present in many tissues in addition to the brain. Calpain I is activated by micromolar concentrations of calcium while calpain II is activated by millimolar concentrations. In the brain, calpain II is the predominant form, but calpain I is found at synaptic endings and is thought to be the form involved in long term potentiation, synaptic plasticity, and cell death Other $Ca^{2+}$ activated cysteine proteases may exist, and the term "calpain" is used to refer to all $Ca^{2+}$ activated cysteine proteases, including calpain I and calpain II. The terms "calpain I" and "calpain II" are used herein to refer to the micromolar and millimolar activated calpains, respectively, as described above. While calpains degrade a wide variety of protein substrates, cytoskeletal proteins seem to be particularly susceptible to attack. In some cases, the products of the proteolytic digestion of these proteins by calpain are distinctive and persistent over time. Since cytoskeletal proteins are major components of certain types of cells, this provides a simple method of detecting calpain activity in cells and tissues. Thus, calpain activation can be measured indirectly by assaying the proteolysis of the cytoskeletal protein spectrin, which produces a large, distinctive and biologically persistent breakdown product when attacked by calpain [Siman, Baudry, and Lynch, *Proc. Natl. Acad. Sci. USA* 81, 3572–3576 (1984); incorporated herein by reference]. Activation of calpains and/or accumulation of breakdown products of cytoskeletal elements has been observed in neural tissues of mammals exposed to a wide variety of neurodegenerative diseases and conditions. For example, these phenomena have been observed following ischemia in gerbils and rats, following stroke in humans, following administration of the toxins kainate, trimethyltin or colchicine in rats, and in human Alzheimer's disease.

Several inhibitors of calpain have been described including peptide aldehydes such as Ac—Leu—Leu—Nle—H and leupeptin (Ac—Leu—Leu—Arg—H), as well as epoxysuccinates such as E-64. These compounds are not especially useful at inhibiting calpain in neural tissue in vivo because they are poorly membrane permeant and, accordingly, are not likely to cross the blood brain barrier very well. Also, many of these inhibitors have poor specificity and will inhibit a wide variety of proteases in addition to calpain. Other classes of compounds which inhibit cysteine proteases include peptide diazomethyl ketone (Rich, D. H., in *Protease Inhibitors*, Barrett A. J., and Salversen, G., Eds., Elsevier, New York, 1986, pp 153–178; incorporated herein by reference). Peptide diazomethyl ketones are potentially carcinogenic and are thought to be poorly membrane permeant and to have low specificity. Thus, no effective therapy has yet been developed for most neurodegenerative diseases and conditions. Millions of individuals suffer from neurodegenerative diseases and thus, there is a need for therapies effective in treating and preventing these diseases and conditions.

Cathepsin B is involved in muscular dystrophy, myocardial tissue damage, tumor metastasis, and bone resorption. In addition, a number of viral processing enzymes, which are essential for viral infection, are cysteine proteases, inhibitors of cysteine proteases would have multiple therapeutic uses.

Serine Proteases

Serine proteases play critical roles in several physiological processes such as digestion, blood coagulation, complement activation, fibrinolysis, viral infection, fertilization, and reproduction. Serine proteases are not only a physiological necessity, but also a potential hazard if they are not controlled. Uncontrolled proteolysis by elastases may cause pancreatitis, emphysema, rheumatoid artritis, bronchial inflammation and adult respiratory distress syndrome. It has been suggested that a new trypsin-like cellular enzyme (tryptase) is involved in the infection of human immunodeficiency virus type 1 [HIV-1; Hattori et al., *FEBS Letters* 248, pp. 48–52 (1989)], which is a causative agent of acquired immunodeficiency syndrome (AIDS). Plasmin is involved in twnor invasiveness, tissue remodeling, blistering, and clot dissociation. Accordingly, specific and selective inhibitors of these proteases should be potent anticoagulants, anti-inflammtory agents, anti-tumor agents and anti-viral agents usefull in the treatment of protease-related diseases [Powers and Harper, *Proteinase Inhibitors*, pp 55–152, Barrett and Salvesen, eds., Elsevier, (1986); incorporated herein by reference]. In vitro proteolysis by chymotrypsin, trypsin or the elastase family is a serious problem in the production, purification, isolation, transport or storage of peptides and proteins.

Elastase inhibitors are anti-inflammatory agents which can be used to treat elastase-associated inflammation including rheumatoid arthritis and emphysema Although the naturally occurring protease inhibitor, α1-protease inhibitor (α1-PI) has been used to treat patients with emphysema, this protein inhibitor is not widely used clinically due to the high dosage needed for treatment and the difficulty of producing large quantities. Therefore, small molecular weight elastase inhibitors are needed for therapy. Other low molecular weight elastase inhibitors have utility for the treatment of emphysema and inflammation (see: 1-carpapenem-3-carboxylic esters as anti-inflammatory agents, U.S. Pat. No. 4,493,839; N-carboxyl-thienamycin esters and analogs thereof as anti-inflammatory agents, U.S. Pat. No. 4,495,197; incorporated herein by reference).

Anticoagulants and antithrombotic drugs are used in a variety of thrombotic disorders. The 1990 Physician's Desk Reference lists several anticoagulant drugs (heparin, protamine sulfate and warfarin), a few antiplatelet drugs (aspirin) and several thrombolytic agents. Heparin and warfarin are commonly used clinically for prevention and treatment of venous thrombosis and pulmonary embolism. Heparin inhibits the blood coagulation activity by accelerating the binding of natural plasma protease inhibitor antithrombin III with coagulation factors, and warfarin acts as a vitamin K antagonist and inhibits the synthesis of coagulation factors. None of the anticoagulant drugs, antithrombotic drugs, fibrinolytic agents and antiplatelet drugs are highly effective in all clinical situations and many induce side reactions [Von Kaulla, *Burger's Medicinal Chemistry, Part II*, pp 1081–1132, Wolff, ed., (1979); incorporated herein by reference]. Coagulation disorders such as disseminated intravascular coagulation, bleeding complications of medical and surgical procedures and bleeding complications of systemic illness are still difficult to manage [Ingram, Brozovic and Slater, *Bleeding Disorders*, pp 1–413, Blackwell Scientific Publications, (1982); incorporated herein by reference]. In the treatment of patients with coagulation problems, anticoagulant or antithrombotic agents of diverse mechanisms are urgently sought in order to provide better medical care. Inhibitors for the trypsin-like enzymes involved in blood coagulation are useful anticoagulants in vivo [see for example: H—D—Phe—Pro—Arg—$CH_2Cl$, Hanson and Harker, *Proc. Natl. Acad. Sci.* 85, 3184–3188 (1988); 7-Amino-4-chloro-3-(3-isothiureidopropoxy) isocoumarin (ACITIC), Oweida, Ku, Lumsden, Kam, and Powers, *Thrombos. Res.* 58, 191–197 (1990); incorporated herein by reference].

Ketoesters

A few amino acid and peptide ketoesters and ketoacids have been previously reported. Cornforth and Comforth [*J. Chem. Soc.*, 93–96 (1953); incorporated herein by reference] report the synthesis of the ketoacids $PhCH_2CO$—Gly—CO—OH and Ac—Gly—CO—OH upon hydrolysis of heterocyclic molecules. Charles et al. [*J. Chem. Soc. Perkin I*, 1139–1146 (1980); incorporated herein by reference] use ketoesters for the synthesis of bicyclic heterocycles. They report the synthesis of n—BuCO—Ala—CO—OEt, PrCO—Ala—CO—OEt, cyclopentylCO—Ala—CO—OEt, PrCO—PhGly—CO—OEt, and Bz—Ala—CO—OEt. Hori et al. [*Peptides: Structure and Function-Proceedings of the Ninth American Peptide Symposium* (Deber, Hruby, and Kopple, Eds.) Pierce Chemical Co., pp 819–822 (1985); incorporated herein by reference] report Bz—Ala—CO—OEt, Bz—Ala—CO—OH, Z—Ala—Ala—Abu—CO—OEt, Z—Ala—Ala—Abu—CO—OBzl, and Z—Ala—Ala—Ala—Ala—CO—OEt (Abu=2-aminobutanoic acid or α-aminobutyric acid) and report that these compounds inhibit elastase. Trainer [*Trends Pharm. Sci.* 8, 303–307 (1987); incorporated herein by reference] comments on one of this compounds. Burkhart, J., Peet, N. P., and Bey, P. [*Tetrahedron Lett.* 29, 3433–3436 (1988); incorporated herein by reference] report the synthesis of Z—Val—Phe—CO—OMe and Bz—Phe—CO—OMe.

Mehdi et al., [*Biochem. Biophys. Res. Comm.* 166, 595–600 (1990); incorporated herein by reference] report the inhibition of human neutrophil elastase and cathepsin G by peptide α-ketoesters. Angelastro et al., [*J. Med. Chem.* 33, 13–16 (1990); incorporated herein by reference] report some α-ketoesters which are inhibitors of calpain and chymotrypsin. Hu and Abeles [*Arch. Biochem. Biophys.* 281, 271–274 (1990)]; incorporated herein by reference] report some peptidyl α-ketoamides and α-ketoacids which are inhibitors of cathepsin B and papain. Peet et al. [*J. Med. Chem.* 33, 394–407 (1990); incorporated herein by reference] report some peptidyl α-ketoesters which are inhibitors of porcine pancreatic elastase, human neutrophil elastase, and rat & human neutrophil cathepsin G.

Ketoamides

A single peptide ketoamide is reported in the literature by Hu and Abeles [*Arch. Biochem. Biophys.* 281, 271–274 (1990)]. This compound Z—Phe—$NHCH_2CO$—CO—NH—Et or Z—Phe—Gly—CO—NH—Et is reported to be an inhibitor of papain ($K_I$=1.5 μM) and cathepsin B ($K_I$=4 μM).

SUMMARY OF THE INVENTION

We have discovered that peptide and amino acid α-ketoamide derivatives are a novel group of inhibitors for serine proteases and cysteine proteases. Inhibitors are compounds that reduce or eliminate the catalytic activity of the enzyme. We have discovered that peptide α-ketoamide derivatives, which have an amino acid sequence similar to that of good substrates for a particular protease, are good inhibitors for that protease. Thus, we are able to predict the structures of new inhibitors for other serine and cysteine proteases based on knowledge of their substrate specificities.

We have discovered some peptide α-ketoamide derivatives which are specific inhibitors for chymotrypsin. Chymotrypsin and chymotrypsin-like enzymes hydrolyze peptide bonds where $P_1$ amino acid is Trp, Tyr, Phe, Met, Leu or other amino acid residues which contain aromatic or large alkyl side chains. Inhibitors with these residues at $P_1$ are good chymotrypsin and chymase inhibitors. Trypsin and trypsin-like enzymes normally cleave peptide bonds in proteins and peptides where the amino acid residue on the carbonyl side of the split bond ($P_1$ residue) is Lys or Arg. We show that peptide α-ketoamide derivatives which have Lys or Arg at $P_1$ will be good inhibitors for these enzymes. Elastase and elastase-like enzymes cleave peptide bonds where the $P_1$ amino acid is Ala, Val, Ser, Leu and other similar amino acids. We shown that inhibitors with these residues at $P_1$ are good elastase inhibitors. All of the above enzymes have extensive secondary specificity and recognize amino acid residues removed from the $P_1$ residue.

The peptide α-ketoamide derivatives are also novel and potent inhibitors of cysteine proteases including calpains and cathepsin B. The calpain inhibitors are useful for treatment of various neurodegenerative diseases and conditions, including ischemia, stroke, and Alzheimer's disease.

The new protease inhibitors, especially the elastase inhibitors, trypsin inhibitors, and chymase inhibitors are useful for controlling tissue damage and various inflammatory conditions mediated by proteases such as blistering. The inhibitors for blood coagulation enzymes will be useful anticoagulants and could be used to treat thrombosis.

The peptide and amino acid α-ketoamide derivatives are also useful in vitro for inhibiting trypsin, elastase, chymotypsin and other serine proteases of similar specificity, and for inhibiting serine proteases in general. The inhibitors can be used to identify new proteolytic enzymes encountered in research. They can also be used in research and industrially to prevent undesired proteolysis that occurs during the production, isolation, purification, transport and storage of valuable peptides and proteins. Such proteolysis often destroys or alters the activity and/or function of the peptides and proteins. Uses would include the addition of the inhibitors to antibodies, enzymes, plasma proteins, tissue extracts or other proteins and peptides which are widely sold for use in clinical analyses, biomedical research, and for many other reasons. For some uses a specific inhibitor would be desirable, while in other cases, an inhibitor with general specificity would be preferred.

DETAILED DESCRIPTION OF THE INVENTION

Peptide α-ketoamides are transition state analog inhibitors for serine proteases and cysteine proteases. Peptide α-ketoamides containing hydrophobic amino acid residues in the $P_1$ site have been found to be excellent inhibitors of serine proteases including porcine pancreatic elastase and bovine chymotrypsin. We show that peptide α-ketoamides containing amino acid residues with cationic side chains in the $P_1$ site will be excellent inhibitors of several serine proteases including bovine trypsin, bovine thrombin, human plasma kallikrein, porcine pancreatic kallikrein, human factor XIa and human plasmin. Peptide α-ketoamides containing amino acid residues with hydrophobic side chain at the $P_1$ site have also been found to be excellent inhibitors of several cysteine proteases including papain, cathepsin B, calpain I, and calpain II. These structures may be used in vivo to treat diseases such as emphysema, adult respiratory distress syndrome, rheumatoid arthritis and pancreatitis which result from uncontrolled proteolysis by elastase, chymotrypsin, trypsin and related serine proteases. These inhibitors may be used in vitro to prevent proteolysis which occurs in the process of production, isolation, purification, storage or transport of peptides and proteins. These inhibitors may be useful as therapeutic agents for treatment of neurodegeneration, viral infections, muscular dystrophy, myocardial tissue damage, tumor metastasis, and bone resorption.

The novel class of dipeptide α-ketoamides have the following structural formula:

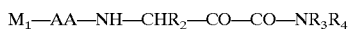

or a pharmaceutically acceptable salt, wherein $M_1$ represents H, $NH_2$—CO, $NH_2$—CS—, $NH_2$—$SO_2$—, X—NH—CO—, $X_2N$—CO—, X—NH—CS—, $X_2N$—CS—, X—NH—$SO_2$—, $X_2N$—$SO_2$—, X—CO—, X—CS—, X—$SO_2$—, X—O—CO—, or X—O—CS—;

X is selected from the group consisting of $C_{1-10}$ alkyl, $C_{1-10}$ fluoroalkyl, $C_{1-10}$ alkyl substituted with J, $C_{1-10}$ fluoroalkyl substituted with J, 1-admantyl, 9-fluorenyl, phenyl, phenyl substituted with K, phenyl disubstituted with K, phenyl trisubstituted with K, naphthyl, naphthyl substituted with K, naphthyl disubstituted with K, naphthyl trisubstituted with K, $C_{1-10}$ alkyl with an attached phenyl group, $C_{1-10}$ alkyl with two attached phenyl groups, $C_{1-10}$ alkyl with an attached phenyl group substituted with K, $C_{1-10}$ alkyl with two attached phenyl groups substituted with K, $C_{1-10}$ alkyl with an attached phenoxy group, and $C_{1-10}$ alkyl with an attached phenoxy group substituted with K on the phenoxy group;

J is selected from the group consisting of halogen, COOH, OH, CN, $NO_2$, $NH_2$, $C_{1-10}$ alkoxy, $C_{1-10}$ alkylamine, $C_{2-12}$ dialkylamine, $C_{1-10}$ alkyl—O—CO—, $C_{1-10}$ alkyl—O—CO—NH—, and $C_{1-10}$ alkyl—S—;

K is selected from the group consisting of halogen, $C_{1-10}$ alkyl, $C_{1-10}$ perfluoroalkyl, $C_{1-10}$ alkoxy, $NO_2$, CN, OH, $CO_2H$, amino, $C_{1-10}$ alkylamino, $C_{2-12}$ dialkylamino, $C_1$–$C_{10}$ acyl, and $C_{1-10}$ alkoxy—CO—, and $C_{1-10}$ alkyl—S—;

AA is a side chain blocked or unblocked amino acid with the L configuration, D configuration, or no chirality at the α-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, beta-alanine, norleucine, norvaline, alpha-aminobutyric acid, epsilon-aminocaproic acid, citrulline, hydroxyproline, ornithine, homoarginine, sarcosine, indoline 2-carboxylic acid, 2-azetidinecarboxylic acid, pipecolinic acid (2-piperidine carboxylic acid), O-methylserine, O-ethylserine, S-methylcysteine, S-ethylcysteine, S-benzylcysteine, $NH_2$—CH($CH_2CHEt_2$)—COOH, alpha-aminoheptanoic acid, $NH_2$—CH($CH_2$-1-napthyl)—COOH, $NH_2$—CH($CH_2$-2-napthyl)—COOH, $NH_2$—CH($CH_2$-cyclohexyl)—COOH, $NH_2$—CH($CH_2$-cyclopentyl)—COOH, $NH_2$—CH($CH_2$-cyclobutyl)—COOH, $NH_2$—CH($CH_2$-cyclopropyl)—COOH, trifluoroleucine, and hexafluoroleucine;

$R_2$ is selected from the group consisting of $C_{1-8}$ branched and unbranched alkyl, $C_{1-8}$ branched and unbranched cyclized alkyl, and $C_{1-8}$ branched and unbranched fluoroalkyl;

R$_3$ and R$_4$ are selected independently from the group consisting of H, C$_{1-20}$ alkyl, C$_{3-20}$ cyclized alkyl, C$_{1-20}$ alkyl with a phenyl group attached to the C$_{1-20}$ alkyl, C$_{3-20}$ cyclized alkyl with an attached phenyl group, C$_{1-20}$ alkyl with an attached phenyl group substituted with K, C$_{1-20}$ alkyl with an attached phenyl group disubstituted with K, C$_{1-20}$ alkyl with an attached phenyl group trisubstituted with K, C$_{3-20}$ cyclized alkyl with an attached phenyl group substituted with K, C$_{1-10}$ alkyl with a morpholine [—N(CH$_2$CH$_2$)O] ring attached through nitrogen to the alkyl, C$_{1-10}$ alkyl with a piperidine ring attached through nitrogen to the alkyl, C$_{1-10}$ alkyl with a pyrrolidine ring attached through nitrogen to the alkyl, C$_{1-20}$ alkyl with an OH group attached to the alkyl, —CH$_2$CH$_2$OCH$_2$CH$_2$OH, C$_{1-10}$ with an attached 4-pyridyl group, C$_{1-10}$ with an attached 3-pyridyl group, C$_{1-10}$ with an attached 2-pyridyl group, C$_{1-10}$ with an attached cyclohexyl group, —NH—CH$_2$CH$_2$—(4-hydroxyphenyl), and —NH—CH$_2$CH$_2$-(3-indolyl).

The novel class of dipeptide α-ketoamides also have the following structural formula:

M$_1$—AA$_2$—AA$_1$—CO—NR$_3$R$_4$ or a pharmaceutically acceptable salt, wherein M$_1$ represents H, NH$_2$—CO—, NH$_2$—CS—, NH$_2$—SO$_2$—, X—NH—CO—, X$_2$N—CO—, X—NH—CS—, X$_2$N—CS—, X—NH—SO$_2$—, X$_2$N—SO$_2$—, X—CO—, X—CS—, X—SO$_2$—, X—O—CO—, or X—O—CS—;

X is selected from the group consisting of C$_{1-10}$ alkyl, C$_{1-10}$ fluoroalkyl, C$_{1-10}$ alkyl substituted with J, C$_{1-10}$ fluoroalkyl substituted with J, 1-admantyl, 9-fluorenyl, phenyl, phenyl substituted with K, phenyl disubstituted with K, phenyl trisubstituted with K, naphthyl, naphthyl substituted with K, naphthyl disubstituted with K, naphthyl trisubstituted with K, C$_{1-10}$ alkyl with an attached phenyl group, C$_{1-10}$ alkyl with two attached phenyl groups, C$_{1-10}$ alkyl with an attached phenyl group substituted with K, C$_{1-10}$ alkyl with two attached phenyl groups substituted with K, C$_{1-10}$ alkyl with an attached phenoxy group, and C$_{1-10}$ alkyl with an attached phenoxy group substituted with K on the phenoxy group;

J is selected from the group consisting of halogen, COOH, OH, CN, NO$_2$, NH$_2$, C$_{1-10}$ alkoxy, C$_{1-10}$ alkylamine, C$_{2-12}$ dialkylamine, C$_{1-10}$ alkyl—O—CO—, C$_{1-10}$ alkyl—O—CO—NH—, and C$_{1-10}$ alkyl—S—;

K is selected from the group consisting of halogen, C$_{1-10}$ alkyl, C$_{1-10}$ perfluoroalkyl, C$_{1-10}$ alkoxy, NO$_2$, CN, OH, CO$_2$H, amino, C$_{1-10}$ alkylamino, C$_{2-12}$ dialkylamino, C$_1$–C$_{10}$ acyl, and C$_{1-10}$ alkoxy—CO—, and C$_{1-10}$ alkyl—S—;

AA$_1$ is a side chain blocked or unblocked amino acid with the L configuration, D configuration, or no chirality at the a-carbon selected from the group consisting of alanine, valine, leucine, isoleucine, proline, methionine, methionine sulfoxide, phenylalanine, tryptophan, serine, threonine, cysteine, tyrosine, asparagine, glutamine, aspartic acid, glutamic acid, lysine, arginine, histidine, phenylglycine, beta-alanine, norleucine, norvaline, alpha-aminobutyric acid, epsilon-aminocaproic acid, citrulline, hydroxyproline, ornithine, homoarginine, sarcosine, indoline 2-carboxylic acid, 2-azetidinecarboxylic acid, pipecolinic acid (2-piperidine carboxylic acid), O-methylserine, O-ethylserine, S-methylcysteine, S-ethylcysteine, S-benzylcysteine, NH$_2$—CH(CH$_2$CHEt$_2$)—COOH, alpha-aminoheptanoic acid, NH$_2$—CH(CH$_2$-1-napthyl)—COOH, NH$_2$—CH(CH$_2$-2-napthyl)—COOH, NH$_2$—CH(CH$_2$-cyclohexyl)—COOH, NH2—CH(CH$_2$-cyclopentyl)—COOH, NH$_2$—CH(CH$_2$-cyclobutyl)—COOH, NH$_2$—CH(CH$_2$-cyclopropyl)—COOH, trifluoroleucine, and hexafluoroleucine;

AA$_2$ is a side chain blocked or unblocked amino acid with the L configuration, D configuration, or no chirality at the α-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, beta-alanine, norleucine, norvaline, alpha-aminobutyric acid, epsilon-aminocaproic acid, citrulline, hydroxyproline, ornithine, homoarginine, sarcosine, indoline 2-carboxylic acid, 2-azetidinecarboxylic acid, pipecolinic acid (2-piperidine carboxylic acid), O-methylserine, O-ethylserine, S-methylcysteine, S-ethylcysteine, S-benzylcysteine, NH$_2$—CH(CH$_2$CHEt$_2$)—COOH, alpha-aminoheptanoic acid, NH$_2$—CH(CH$_2$-1-napthyl)—COOH, NH$_2$—CH(CH$_2$-2-napthyl)—COOH, NH$_2$—CH(CH$_2$-cyclohexyl)—COOH, NH$_2$—CH(CH$_2$-cyclopentyl)—COOH, NH$_2$—CH(CH$_2$-cyclobutyl)—COOH, NH$_2$—CH(CH$_2$-cyclopropyl)—COOH, trifluoroleucine, and hexafluoroleucine;

R$_3$ and R$_4$ are selected independently from the group consisting of H, C$_{1-20}$ alkyl, C$_{3-20}$ cyclized alkyl, C$_{1-20}$ alkyl with a phenyl group attached to the C$_{1-20}$ alkyl, C$_{3-20}$ cyclized alkyl with an attached phenyl group, C$_{1-20}$ alkyl with an attached phenyl group substituted with K, C$_{1-20}$ alkyl with an attached phenyl group disubstituted with K, C$_{1-20}$ alkyl with an attached phenyl group trisubstituted with K, C$_{3-20}$ cyclized alkyl with an attached phenyl group substituted with K, C$_{1-10}$ alkyl with a morpholine [—N(CH$_2$CH$_2$)O] ring attached through nitrogen to the alkyl, C$_{1-10}$ alkyl with a piperidine ring attached through nitrogen to the alkyl, C$_{1-10}$ alkyl with a pyrrolidine ring attached through nitrogen to the alkyl, C$_{1-20}$ alkyl with an OH group attached to the alkyl, —CH$_2$CH$_2$OCH$_2$CH$_2$OH, C$_{1-10}$ with an attached 4-pyridyl group, C$_{1-10}$ with an attached 3-pyridyl group, C$_{1-10}$ with an attached 2-pyridyl group, C$_{1-10}$ with an attached cyclohexyl group, —NH—CH$_2$CH$_2$-(4-hydroxyphenyl), and —NH—CH$_2$CH$_2$-(3-indolyl).

The novel class of tripeptide α-ketoamides have the following structural formula:

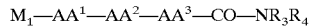

M$_1$—AA$^1$—AA$^2$—AA$^3$—CO—NR$_3$R$_4$ or a pharmaceutically acceptable salt, wherein M$_1$ represents H, NH$_2$—CO—, NH$_2$—CS—, NH$_2$—SO$_2$—, X—NH—CO—, X$_2$N—CO—, X—NH—CS—, X$_2$N—CS—, X—NH—SO$_2$—, X$_2$N—SO$_2$—, X—CO—, X—CS—, X—SO$_2$—, X-O—CO—, or X—O—CS—;

X is selected from the group consisting of C$_{1-10}$ alkyl, C$_{1-10}$ fluoroalkyl, C$_{1-10}$ alkyl substituted with J, C$_{1-10}$ fluoroalkyl substituted with J, 1-admantyl, 9-fluorenyl, phenyl, phenyl substituted with K, phenyl disubstituted with K, phenyl trisubstituted with K, naphthyl, naphthyl substituted with K, naphthyl disubstituted with K, naphthyl trisubstituted with K, C$_{1-10}$ alkyl with an attached phenyl group, C$_{1-10}$ alkyl with two attached phenyl groups, C$_{1-10}$ alkyl with an attached phenyl group substituted with K, C$_{1-10}$ alkyl with two attached phenyl groups substituted with K, C$_{1-10}$ alkyl with an attached phenoxy group, and C$_{1-10}$ alkyl with an attached phenoxy group substituted with K on the phenoxy group;

J is selected from the group consisting of halogen, COOH, OH, CN, NO$_2$, NH$_2$, C$_{1-10}$ alkoxy, C$_{1-10}$ alkylamine, C$_{2-12}$ dialkylamine, C-$_{1-10}$ alkyl—O—CO—, C$_{1-10}$ alkyl—O—CO—NH—, and C$_{1-10}$ alkyl—S—;

K is selected from the group consisting of halogen, $C_{1-10}$ alkyl, $C_{1-10}$ perfluoroalkyl, $C_{1-10}$ alkoxy, $NO_2$, CN, OH, $CO_2H$, amino, $C_{1-10}$ alkylamino, $C_{2-12}$ dialkylamino, $C_{1-10}$ acyl, and $C_{1-10}$ alkoxy—CO—, and $C_{1-10}$ alkyl—S—;

$AA^1$, $AA^2$, and $AA^3$ are the same or different and are side chain blocked or unblocked amino acids with the L configuration, D configuration, or no chirality at the a-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, beta-alanine, norleucine, norvaline, alpha-aminobutyric acid, epsilon-aminocaproic acid, citrulline, hydroxyproline, ornithine, homoarginine, sarcosine, indoline 2-carboxylic acid, 2-azetidinecarboxylic acid, pipecolinic acid (2-piperidine carboxylic acid), O-methylserine, O-ethylserine, S-methylcysteine, S-ethylcysteine, S-benzylcysteine, $NH_2$—$CH(CH_2CHEt_2)$—COOH, alpha-aminoheptanoic acid, $NH_2$—$CH(CH_2$-1-napthyl)—COOH, $NH_2$—$CH(CH_2$-2-napthyl)—COOH, $NH_2$—$CH(CH_2$-cyclohexyl)—COOH, $NH_2$—$CH(CH_2$-cyclopentyl)—COOH, $NH_2$—$CH(CH_2$-cyclobutyl)—COOH, $NH_2$—$CH(CH_2$-cyclopropyl)—COOH, trifluoroleucine, and hexafluoroleucine;

$R_3$ and $R_4$ are selected independently from the group consisting of H, $C_{1-20}$ alkyl, $C_{3-20}$ cyclized alkyl, $C_{1-20}$ alkyl with a phenyl group attached to the $C_{1-20}$ alkyl, $C_{3-20}$ cyclized alkyl with an attached phenyl group, $C_{1-20}$ alkyl with an attached phenyl group substituted with K, $C_{1-20}$ alkyl with an attached phenyl group disubstituted with K, $C_{1-20}$ alkyl with an attached phenyl group trisubstituted with K, $C_{3-20}$ cyclized alkyl with an attached phenyl group substituted with K, $C_{1-10}$ alkyl with a morpholine [—N($CH_2CH_2$)O] ring attached through nitrogen to the alkyl, $C_{1-10}$ alkyl with a piperidine ring attached through nitrogen to the alkyl, $C_{1-10}$ alkyl with a pyrrolidine ring attached through nitrogen to the alkyl, $C_{1-20}$ alkyl with an OH group attached to the alkyl, —$CH_2CH_2OCH_2CH_2OH$, $C_{1-10}$ with an attached 4-pyridyl group, $C_{1-10}$ with an attached 3-pyridyl group, $C_{1-10}$ with an attached 2-pyridyl group, $C_{1-10}$ with an attached cyclohexyl group, —NH—$CH_2CH_2$-(4-hydroxyphenyl), and —NH—$CH_2CH_2$-(3-indolyl).

The novel class of tetrapeptide α-ketoamides have the following structural formula:

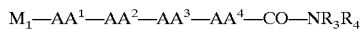

$$M_1-AA^1-AA^2-AA^3-AA^4-CO-NR_3R_4$$

or a pharmaceutically acceptable salt, wherein $M_1$ represents H, $NH_2$—CO—, $NH_2$—CS—, $NH_2$—$SO_2$—, X—NH—CO—, $X_2N$—CO—, X—NH—CS—, $X_2N$—CS—, X—NH—$SO_2$—, $X_2N$—$SO_2$—, X—CO—, X—CS—, X—$SO_2$—, X—O—CO—, or X—O—CS—;

X is selected from the group consisting of $C_{1-10}$ alkyl, $C_{1-10}$ fluoroalkyl, $C_{1-10}$ alkyl substituted with J, $C_{1-10}$ fluoroalkyl substituted with J, 1-admantyl, 9-fluorenyl, phenyl, phenyl substituted with K, phenyl disubstituted with K, phenyl trisubstituted with K, naphthyl, naphthyl substituted with K, naphthyl disubstituted with K, naphthyl trisubstituted with K, $C_{1-10}$ alkyl with an attached phenyl group, $C_{1-10}$ alkyl with two attached phenyl groups, $C_{1-10}$ alkyl with an attached phenyl group substituted with K, $C_{1-10}$ alkyl with two attached phenyl groups substituted with K, $C_{1-10}$ alkyl with an attached phenoxy group, and $C_{1-10}$ alkyl with an attached phenoxy group substituted with K on the phenoxy group;

J is selected from the group consisting of halogen, COOH, OH, CN, $NO_2$, $NH_2$, $C_{1-10}$ alkoxy, $C_{1-10}$ alkylamine, $C_{2-12}$ dialkylamine, $C_{1-10}$ alkyl—O—CO—, $C_{1-10}$ alkyl—O—CO—NH—, and $C_{1-10}$ alkyl—S—;

K is selected from the group consisting of halogen, $C_{1-10}$ alkyl, $C_{1-10}$ perfluoroalkyl, $C_{1-10}$ alkoxy, $NO_2$, CN, OH, $CO_2H$, amino, $C_{1-10}$ alkylamino, $C_{2-12}$ dialkylamino, $C_1$–$C_{10}$ acyl, and $C_{1-10}$ alkoxy—CO—, and $C_{1-10}$ alkyl—S—;

$AA^1$, $AA^2$, and $AA^3$ are the same or different and are side chain blocked or unblocked amino acids with the L configuration, D configuration, or no chirality at the a-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, beta-alanine, norleucine, norvaline, alpha-aminobutyric acid, epsilon-aminocaproic acid, citrulline, hydroxyproline, ornithine, homoarginine, sarcosine, indoline 2-carboxylic acid, 2-azetidinecarboxylic acid, pipecolinic acid (2-piperidine carboxylic acid), O-methylserine, O-ethylserine, S-methylcysteine, S-ethylcysteine, S-benzylcysteine, $NH_2$—$CH(CH_2CHEt_2)$—COOH, alpha-aminoheptanoic acid, $NH_2$—$CH(CH_2$-1-napthyl)—COOH, $NH_2$—$CH(CH_2$-2-napthyl)—COOH, $NH_2$—$CH(CH_2$-cyclohexyl)—COOH, $NH_2$—$CH(CH_2$-cyclopentyl)—COOH, $NH_2$—$CH(CH_2$-cyclobutyl)—OOH, $NH_2$—$CH(CH_2$-cyclopropyl)—COOH, trifluoroleucine, and hexafluoroleucine;

$R_3$ and $R_4$ are selected independently from the group consisting of H, $C_{1-20}$ alkyl, $C_{3-20}$ cyclized alkyl, $C_{1-20}$ alkyl with a phenyl group attached to the $C_{1-20}$ alkyl, $C_{3-20}$ cyclized alkyl with an attached phenyl group, $C_{1-20}$ alkyl with an attached phenyl group substituted with K, $C_{1-20}$ alkyl with an attached phenyl group disubstituted with K, $C_{1-20}$ alkyl with an attached phenyl group trisubstituted with K, $C_{3-20}$ cyclized alkyl with an attached phenyl group substituted with K, $C_{1-10}$ alkyl with a morpholine [—N($CH_2CH_2$)O] ring attached through nitrogen to the alkyl, $C_{1-10}$ alkyl with a piperidine ring attached through nitrogen to the alkyl, $C_{1-10}$ alkyl with a pyrrolidine ring attached through nitrogen to the alkyl, $C_{1-20}$ alkyl with an OH group attached to the alkyl, —$CH_2CH_2OCH_2CH_2OH$, $C_{1-10}$ with an attached 4-pyridyl group, $C_{1-10}$ with an attached 3-pyridyl group, $C_{1-10}$ with an attached 2-pyridyl group, $C_{1-10}$ with an attached cyclohexyl group, —NH—$CH_2CH_2$-(4-hydroxyphenyl), and —NH—$CH_2CH_2$-(3-indolyl).

The novel class of amino acid α-ketoamides have the following structural formula:

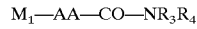

$$M_1-AA-CO-NR_3R_4$$

or a pharmaceutically acceptable salt, wherein $M_1$ represents H, $NH_2$—CO—, $NH_2$—CS—, $NH_2$—$SO_2$—, X—NH—CO—, $X_2N$—CO—, X—NH—CS—, $X_2N$—CS—, X—NH—$SO_2$—, $X_2N$-$S0_2$—, X—CO—, X—CS—, X—$SO_2$—, X—O—CO—, or X—O—CS—;

X is selected from the group consisting of $C_{1-10}$ alkyl, $C_{1-10}$ fluoroalkyl, $C_{1-10}$ alkyl substituted with J, $C_{1-10}$ fluoroalkyl substituted with J, 1-admantyl, 9-fluorenyl, phenyl, phenyl substituted with K, phenyl disubstituted with K, phenyl trisubstituted with K, naphthyl, naphthyl substituted with K, naphthyl disubstituted with K, naphthyl trisubstituted with K, $C_{1-10}$ alkyl with an attached phenyl group, $C_{1-10}$ alkyl with two attached phenyl groups, $C_{1-10}$ alkyl with an attached phenyl group substituted with K, $C_{1-10}$ alkyl with two attached phenyl groups substituted with K, $C_{1-10}$ alkyl with an attached phenoxy group, and $C_{1-10}$ alkyl with an attached phenoxy group substituted with K on the phenoxy group;

J is selected from the group consisting of halogen, COOH, OH, CN, $NO_2$, $NH_2$, $C_{1-10}$ alkoxy, $C_{1-10}$ alkylamine, $C_{2-12}$ dialkylamine, $C_{1-10}$ alkyl—O—CO—, $C_{1-10}$ alkyl—O—CO—NH—, and $C_{1-10}$ alkyl—S—;

K is selected from the group consisting of halogen, $C_{1-10}$ alkyl, $C_{1-10}$ perfluoroalkyl, $C_{1-10}$ alkoxy, $NO_2$, CN, OH, $CO_2H$, amino, $C_{1-10}$ alkylamino, $C_{2-12}$ dialkylamino, $C_1$–$C_{10}$ acyl, and $C_{1-10}$ alkoxy—CO—, and $C_{1-10}$ alkyl—S—;

AA is a side chain blocked or unblocked amino acid with the L configuration, D configuration, or no chirality at the α-carbon selected from the group consisting of alanine, valine, leucine, isoleucine, proline, methionine, methionine sulfoxide, phenylalanine, tryptophan, glycine, serine, threonine, cysteine, tyrosine, asparagine, glutamine, aspartic acid, glutamic acid, lysine, arginine, histidine, phenylglycine, beta-alanine, norleucine, norvaline, alpha-aminobutyric acid, epsilon-aminocaproic acid, citrulline, hydroxyproline, ornithine, homoarginine, sarcosine, indoline 2-carboxylic acid, 2-azetidinecarboxylic acid, pipecolinic acid (2-piperidine carboxylic acid), O-methylserine, O-ethylserine, S-methylcysteine, S-ethylcysteine, S-benzylcysteine, $NH_2$—$CH(CH_2CHEt_2)$—COOH, alpha-aminoheptanoic acid, $NH_2$—$CH(CH_2$-1-napthyl)—COOH, $NH_2$—$CH(CH_2$-2-napthyl)—COOH, $NH_2$—$CH(CH_2$-cyclohexyl)—COOH, $NH_2$—$CH(CH_2$-cyclopentyl)—COOH, $NH_2$—$CH(CH_2$-cyclobutyl)—COOH, $NH_2$—$CH(CH_2$-cyclopropyl)—COOH, trifluoroleucine, and hexafluoroleucine;

$R_3$ and $R_4$ are selected independently from the group consisting of H, $C_{1-20}$ alkyl, $C_{3-20}$ cyclized alkyl, $C_{1-20}$ alkyl with a phenyl group attached to the $C_{1-20}$ alkyl, $C_{3-20}$ cyclized alkyl with an attached phenyl group, $C_{1-20}$ alkyl with an attached phenyl group substituted with K, $C_{1-20}$ alkyl with an attached phenyl group disubstitured with K, $C_{1-20}$ alkyl with an attached phenyl group trisubstituted with K, $C_{3-20}$ cyclized alkyl with an attached phenyl group substituted with K, $C_{1-10}$ alkyl with a morpholine [—N($CH_2CH_2$)O] ring attached through nitrogen to the alkyl, $C_{1-10}$ alkyl with a piperidine ring attached through nitrogen to the alkyl, $C_{1-10}$ alkyl with a pyrrolidine ring attached through nitrogen to the alkyl, $C_{1-20}$ alkyl with an OH group attached to the alkyl, —$CH_2CH_2OCH_2CH_2OH$, $C_{1-10}$ with an attached 4-pyridyl group, $C_{1-10}$ with an attached 3-pyridyl group, $C_{1-10}$ with an attached 2-pyridyl group, $C_{1-10}$ with an attached cyclohexyl group, —NH—$CH_2CH_2$-(4-hydroxyphenyl), and —NH—$CH_2CH_2$-(3-indolyl).

The following compounds are representatives of the invention:

Z—Leu—Phe—CONH—Et
Z—Leu—Phe—CONH—nPr
Z—Leu—Phe—CONH—nBu
Z—Leu—Phe—CONH—iBu
Z—Leu—Phe—CONH—Bzl
Z—Leu—Phe—CONH—$(CH_2)_2$Ph
Z—Leu—Abu—CONH—Et
Z—Leu—Abu—CONH—nPr
Z—Leu—Abu—CONH—nBu
Z—Leu—Abu—CONH—iBu
Z—Leu—Abu—CONH—Bzl
Z—Leu—Abu—CONH—$(CH_2)_2$Ph
Z—Leu—Abu—CONH—$(CH_2)_3$—$N(CH_2CH_2)_2O$
Z—Leu—Abu—CONH—$(CH_2)_7CH_3$
Z—Leu—Abu—CONH—$(CH_2)_2OH$
Z—Leu—Abu—CONH—$(CH_2)_2O(CH_2)_2OH$
Z—Leu—Abu—CONH—$(CH_2)_{17}CH_3$
Z—Leu—Abu—CONH—$CH_2$—$C_6H_3(OCH_3)_2$
Z—Leu—Abu—CONH—$CH_2$—$C_4H_4N$

Materials and Methods

HEPES, heparin, and A23187 were obtained from Calbiochem. Suc—Leu—Tyr—AMC and chromogenic substrates were obtained from Sigma Calpain I was purified from human erythrocytes according to the method of Kitahara (Kitahara et al., *J. Biochem.* 95, 1759–1766) omitting the Blue-Sepharose step. Calpain II from rabbit muscle and cathepsin B were purchased from Sigma. Papain was purchased from Calbiochem.

Assay of Inhibitory Potency

Peptide α-ketoamides were assayed as reversible enzyme inhibitors. Various concentrations of inhibitors in $Me_2SO$ were added to the assay mixture which contained buffer and substrate. The reaction was started by the addition of the enzyme and the hydrolysis rates were followed spectrophotometrically or fluorimetrically.

Calpain I from human erythrocytes and calpain II from rabbit were assayed using Suc-Leu-Tyr-AMC [Sasaki et al., *J. Biol. Chem.* 259, 12489–12494 (1984); incorporated herein by reference], and the AMC (7-amino-4-methylcoumarin) release was followed fluorimetrically (excitation at 380 nm, and emmision at 460 nm). Calpains were assayed in 25 mM Tris pH=8.0, 10 mM $CaCl_2$. Fluorescence was followed using a Gilson FL-1A fluorometer or a Perkin-Elmer 203 Fluorescence spectrometer. Cathepsin B was assayed in 20 mM sodium acetate pH=5.2, 0.5 mM dithiothreitol using Bz-Phe-Val-Arg-p-nitroanilide as substrate. Alternately, cathepsin B was assayed with Z-Arg-Arg-AFC [Barrett and Kirschke, *Methods Enzymol.* 80, 535–561 (1981); incorporated herein by reference], and the AFC (7-amino-4-trifluoromethylcoumarin) release was followed fluorimetrically (excitation at 400 nm and emmision at 505 nm). Papain was assayed in 100 mM $KPO_4$, 1 mM EDTA, 2.5 mM cysteine pH=6.0 using Bz-Arg-AMC or Bz-Arg-NA [Kanaoka et al., *Chem. Pharm. Bull.* 25, 3126–3128 (1977); incorporated herein by reference] as a substrate. The AMC (7-amino-4-methylcoumarin) release was followed fluorimetrically (excitation at 380 nm, and emmision at 460 nm). Enzymatic hydrolysis rates were measured at various substrate and inhibitor concentrations, and $K_I$ values were determined by either Lineweaver-Burk plots or Dixon plots.

A 0.1 M Hepes, 0.5 M NaCl, pH 7.5 buffer was utilized for human leukocyte elastase (HLE), porcine pancreatic elastase (PPE), chymotrypsin and cathepsin G. A 0.1 Hepes, 0.01 M $CaCl_2$, pH 7.5 buffer was utilized for trypsin, plasmin, and coagulation enzymes. A 50 mM Tris-HCl, 2 mM EDTA, 5 mM cysteine, pH 7.5 was used as a buffer for papain. A 88 mM $KH_2PO4$, 12 mM $Na_2HPO_4$, 1.33 mM EDTA, 2.7 mM cysteine, pH 6.0 solution was used as a buffer for cathepsin B. A 20 mM Hepes, 10 mM $CaCl_2$, 10 mM mercatoethanol, pH 7.2 buffer was utilized for calpain I and calpain II.

HLE and PPE were assayed with MeO—Suc—Ala—Ala—Pro—Val—NA and Suc—Ala—Ala—Ala—NA, respectively [Nakajima et al., *J. Biol. Chem.* 254, 4027–4032 (1979); incorporated herein by reference]. Human leukocyte cathepsin G and chymotrypsin $A_\alpha$ were assayed with Suc-Val-Pro-Phe-NA [Tanaka et al., *Biochemistry* 24, 2040–2047 (1985); incorporated herein by reference]. The hydrolysis of peptide 4-nitroanilides was measured at 410 nm [$\epsilon_{410}$=8800 $M^{-1}cm^{-1}$; Erlanger et al., *Arch. Biochem. Biophys.* 95, pp 271–278 (1961); incorporated herein by reference]. Trypsin, thrombin, human plasma kallikrein, porcine pancreatic kallikrein, human factor XIa, and human plasmin were assayed with Z—Arg—SBzl or Z—Gly—Arg—SBu—i [McRae et al., *Biochemistry* 20, 7196–7206 (1981); incorporated herein by reference]. All peptide thioester hydrolysis rates were measured with assay mixtures containing 4,4'-dithiodipyridine [$\epsilon_{324}$=19800 M$^{-1}$ cm$^{-1}$; Grasetti & Murray, *Arch. Biochem. Biophys.* 119, 41–49 (1967); incorporated herein by reference].

Platelet membrane permeability assay. Calpain-mediated breakdown of spectrin was measured by quantitative densitometry of the calpain-specific 150/155 kDa spectrin fragment doublet [see Siman et al., *Proc. Natl. Acad. Sci USA* 81, 3572–3576 (1984)]. Platelets were isolated by a modification of the method of Ferrell and Martin [*J. Biol. Chem.* 264, 20723–20729 (1989)]. Blood (15–20 ml) was drawn from male Sprague-Dawley rats into 1/10th volume of 100 mM EDTA-citrate, and centrifuged 10 minutes at 2000 rpm in a clinical centrifuge at room temperature. The plasma was resuspended in 15 ml of buffer 1 (136 mM NaCl, 2.7 mM KCl, 0.42 mM NaH$_2$PO$_4$, 12 mM NaHCO$_3$, 2 mM MgCl$_2$, 2 mg/ml BSA (Sigma), 5.6 mM glucose, 22 mM Na$_3$citrate pH 6.5) and platelets were isolated at 2200 rpm at room temperature for 10 minutes. Platelets were washed once in 15 ml buffer 1, then resuspended to 10$^7$ cells/ml in buffer 2 (136 mM NaCl, 2.7 mM KCl, 0.42 mM NaH$_2$PO$_4$, 12 mM NaHCO$_3$, 2 mM MgCl, 1 mg/ml BSA (Sigma), 5.6 mM glucose, 20 mM HEPES (Sigma) pH 7.4) and allowed to "rest" for a minimum of 10 minutes at room temperature before use.

Inhibitors were added from stock solutions made fresh in DMSO. 100 μl platelets, suspended to 10$^7$ cells/ml in buffer 2, were incubated with 1 μl of an inhibitor solution for 5 minutes at room temperature prior to the addition of 2 mM Ca$^{2+}$ and 1 μM A23187. After 10 minutes total exposure to inhibitor (5 minutes exposure to ionophore) at room temperature, platelets were reisolated at 14,000 rpm for 10 sec in a Beckman microfuge, dissolved in SDS-PAGE sample buffer, and heated to 90° C. for 3 minutes.

Samples were subjected to SDS-PAGE in 4–12% gradient mini gels (Novex) and transferred to nitrocellulose (Schleicher and Schuell 0.45 um) by electroblotting. Filters were blocked for 10 minutes in 0.25% gelatin, 1% BSA, 0.25% triton X100, 0.9% NaCl, 10 mM Tris-Cl pH 7.5, incubated overnight in the same solution containing antibody to rat spectrin, washed 3×10 minutes with 10 mM Tris-Cl pH 7.5, 0.5% triton X 100, incubated 4 hours in wash buffer plus alkaline phosphatase conjugated goat anti-rabbit antibody (Biorad), and washed as above. Blots were developed using the Biorad AP conjugate substrate kit. Quantitative densitometry was used to obtain values for the intact spectrin bands and the 150/155 kDa breakdown product doublet.

Structure-Activity Relationships

Table I shows the inhibition constants ($K_I$) for cathepsin B, calpain I, and calpain II. Dipeptide α-ketoamides with Abu and Phe in the P$_1$ site and Leu in the P$_2$ site are potent inhibitors of calpain I and calpain II. Z—Leu—Abu—CONH—Et is a better inhibitor of calpain I than Z—Leu—Phe—CONH—Et by 14 fold. Replacement of the Z group (PhCH$_2$OCO—) by similar groups such as PhCH$_2$CH$_2$CO—, PhCH$_2$CH$_2$SO$_2$—, PhCH$_2$NHCO—, and PhCH$_2$NHCS— would also result in good inhibitor structures. The best inhibitor of calpain II is Z—Leu—Abu—CONH—(CH$_2$)$_2$—Ph. Changing the R$_3$ and R$_4$ groups significantly improves the inhibitory potency toward calpain II. The best dipeptide inhibitors are those which have long alkyl side chains (e.g. Z—Leu—Abu—CONH—(CH$_2$)$_7$CH$_3$), alkyl side chains with phenyl substituted on the alkyl group (e.g. Z—Leu—Abu—CONH—(CH$_2$)$_2$—Ph), or alkyl groups with a morpholine ring substituted on the alkyl group [e.g. Z—Leu—Abu—CONH—(CH$_2$)$_3$-Mpl, Mpl=—N(CH$_2$CH$_2$)$_2$O]. Dipeptide α-ketoamides with a small aliphatic amino acid residue or a Phe in the P$_1$ site are also good inhibitors for cathepsin B. The best inhibitor is Z—Leu—Abu—CONH—Et and replacement of the Z (PhCH$_2$OCO—) by PhCH$_2$CH$_2$CO—, PhCH$_2$CH$_2$SO$_2$—, PhCH$_2$NHCO—, and PhCH$_2$NHCS— would also result in good inhibitor structures.

TABLE I

Inhibition of Cysteine Proteases by Peptide α-Ketoamides.

| | $K_I$ (μM) | | |
|---|---|---|---|
| Peptide α-Ketoamide | Calpain I | Calpain II | Cath B |
| Z-Leu-Abu-CONH-Et | 0.5 | 0.23 | 2.4 |
| Z-Leu-Abu-CONH-nPr | | 0.25 | 8 |
| Z-Leu-Abu-CONH-nBu | 0.2 | | 13 |
| Z-Leu-Abu-CONH-iBu | | 0.14 | 4 |
| Z-Leu-Abu-CONH-Bzl | | 0.35 | 2 |
| Z-Leu-Abu-CONH—(CH$_2$)$_2$-Ph | | 0.022 | |
| Z-Leu-Abu-CONH—(CH$_2$)$_3$-Mpl | | 0.041 | |
| Z-Leu-Abu-CONH—(CH$_2$)$_7$CH$_3$ | | 0.019 | |
| Z-Leu-Abu-CONH—(CH$_2$)$_{17}$CH$_3$ | | | |
| Z-Leu-Abu-CONH—(CH$_2$)$_2$OH | | 0.078 | |
| Z-Leu-Abu-CONH—(CH$_2$)$_2$O(CH$_2$)$_2$OH | 0.16 | | |
| Z-Leu-Phe-CONH-Et | 7.0 | 0.32 | 6 |
| Z-Leu-Phe-CONH-nPr | 15.0 | 0.05 | 3 |
| Z-Leu-Phe-CONH-nBu | | 0.028 | 3 |
| Z-Leu-Phe-CONH-iBu | | 0.065 | 4 |
| Z-Leu-Phe-CONH-Bzl | | 0.046 | |
| Z-Leu-Phe-CONH(CH$_2$)$_2$Ph | | 0.024 | |

Table II shows the inhibition constants ($K_I$) for PP elastase and chymotrypsin. Dipeptide α-ketoamides with Abu in the P$_1$ site are potent inhibitors of PP elastase. The structures with medium sized straight-chain alkyl groups such as n-Pr and n-Bu were better inhibitors than a small alkyl (Et) or a branched alkyl (i-Bu). Dipeptide α-ketoamides with Phe in the P$_1$ site are moderate inhibitors of chymotrypsin. The inhibitor with R$_3$=n-Bu and R$_4$=H was the best in the series. In general the inhibitors were more potent at inhibiting cysteine protease than serine proteases. Extending the peptide chain to tripeptide or tetrapeptide α-ketoamides would improve the inhibitory potency toward serine proteases.

TABLE II

Inhibition of Serine Proteases by Peptide α-Ketoamides.

| | $K_I$ (μM) | |
|---|---|---|
| Peptide α-Ketoamide | Chymotrypsin | PP elastase |
| Z-Leu-Abu-CONH-Et | >150 | 65 |
| Z-Leu-Abu-CONH-nPr | >300 | 2 |
| Z-Leu-Abu-CONH-nBu | >300 | 5 |
| Z-Leu-Abu-CONH-iBu | >300 | 40 |
| Z-Leu-Abu-CONH-Bzl | >300 | |
| Z-Leu-Abu-CONH—(CH$_2$)$_2$-Ph | | |
| Z-Leu-Abu-CONH—(CH$_2$)$_3$-Mpl | | |
| Z-Leu-Abu-CONH—(CH$_2$)$_7$CH$_3$ | | |
| Z-Leu-Abu-CONH—(CH$_2$)$_{17}$CH$_3$ | | |
| Z-Leu-Abu-CONH—(CH$_2$)$_2$OH | | |
| Z-Leu-Abu-CONH—(CH$_2$)$_2$O(CH$_2$)$_2$OH | | |
| Z-Leu-Phe-CONH-Et | 73 | >150 |
| Z-Leu-Phe-CONH-nPr | 18 | >300 |

TABLE II-continued
Inhibition of Serine Proteases by Peptide α-Ketoamides.

| | $K_I$ (μM) | |
|---|---|---|
| Peptide α-Ketoamide | Chymotrypsin | PP elastase |
| Z-Leu-Phe-CONH-nBu | 8 | >100 |
| Z-Leu-Phe-CONH-iBu | 24 | |
| Z-Leu-Phe-CONH-Bzl | | |
| Z-Leu-Phe-CONH(CH$_2$)$_2$Ph | | |

Peptide α-ketoamide were substantially more stable in both plasma and liver than the corresponding peptide α-ketoesters (Table III). The peptide α-ketoamides were also much more effective in the platelet assay. Extending the $R_3$ group to an alkyl group or an alkyl group substituted with a phenyl group increased the membrane permeability of the inhibitors as indicated by increased potency in the platelet assay.

TABLE III
Half-lives in Plasma and in Liver and Activity in the Platelet Assay.

| Peptide α-Ketoamide or Ester | platelet | t½ plasma | t½ liver |
|---|---|---|---|
| Z-Leu-Abu-COOEt | 42 | 2.8 | |
| Z-Leu-Abu-COOn-Bu | 28 | | |
| Z-Leu-Abu-COOBzl | ++ | | |
| Z-Leu-Leu-Abu-COOEt | 40 | | |
| 2-NapSO2-Leu-Leu-Abu-COOEt | 100 | >60 | |
| 2-NapCO-Leu-Leu-Abu-COOEt | | 25 | |
| Tos-Leu-Leu-Abu-COOEt | 30 | 30 | |
| Z-Leu-Abu-COOH | 8 | >60 | >60 |
| Z-Leu-Abu-CONH-Et | 1.5 | >60 | >60 |
| Z-Leu-Abu-CONH-nPr | 70 | >60 | >60 |
| Z-Leu-Abu-CONH-nBu | 2.0 | >60 | >60 |
| Z-Leu-Abu-CONH-iBu | 28 | >60 | |
| Z-Leu-Abu-CONH-Bzl | 1.5 | >60 | >60 |
| Z-Leu-Phe-COOEt | 42 | 7.8 | |
| Z-Leu-Phe-COOnBu | +++ | 7.7 | |
| Z-Leu-Phe-COOBz | ++ | 1.9 | |

TABLE III-continued
Half-lives in Plasma and in Liver and Activity in the Platelet Assay.

| Peptide α-Ketoamide or Ester | platelet | t½ plasma | t½ liver |
|---|---|---|---|
| Z-Leu-Leu-Phe-COOEt | ++ | | |
| Z-Leu-Phe-COOH | 6.5 | >60 | >60 |
| Z-Leu-Phe-CONH-Et | 1.7 | >60 | >60 |
| Z-Leu-Phe-CONH-nPr | 24 | >60 | >60 |
| Z-Leu-Phe-CONH-nBu | 38 | >60 | >60 |
| Z-Leu-Phe-CONH-iBu | 22 | >60 | |
| Z-Leu-Phe-CONH-Bzl | | | |
| Z-Leu-Phe-CONH(CH$_2$)$_2$Ph | 3.0 | >60 | |
| Z-Leu-Nle-COOEt | 20 | 3.7 | |
| Z-Leu-Nva-COOEt | 40 | 2.8 | |
| Z-Leu-Met-COOEt | + | 8 | |

(+++=excellent activity; ++=good activity, +=moderate activity; quantitiative measurements not yet complete)

Inhibition Mechanism

A crystal structure of one α-ketoester bound into the active site of porcine pancreatic elastase has been completed and a schematic drawing of the interactions observed is shown below. The active site Ser-195 oxygen of the enzyme has added to the carbonyl group of the ketoester to form a tetrahedral intermediate which is stabilized by interactions with the oxyanion hole. This structure resembles the tetrahedral intermediate involved in peptide bond hydrolysis and proves that α-ketoesters are transition-state analogs. His-57 is hydrogen bonded to the carbonyl group of the ester functional group, the peptide backbone on a section of PPE's backbone hydrogen bonds to the inhibitor to form a β-sheet, and the benzyl ester is directed toward the S' subsites. The side chain of the $P_1$ amino acid residue is located in the $S_1$ pocket of the enzyme. Interactions with ketoamides would be similar except for that there would be the possibility of forming an additional hydrogen bond with the NH group of the ketoamide functional group if $R_3$ or $R_4$ was H. If $R_3$ and/or $R_4$ are longer substutuents, then they would make favorable interactions with the S' subsites of the enzyme.

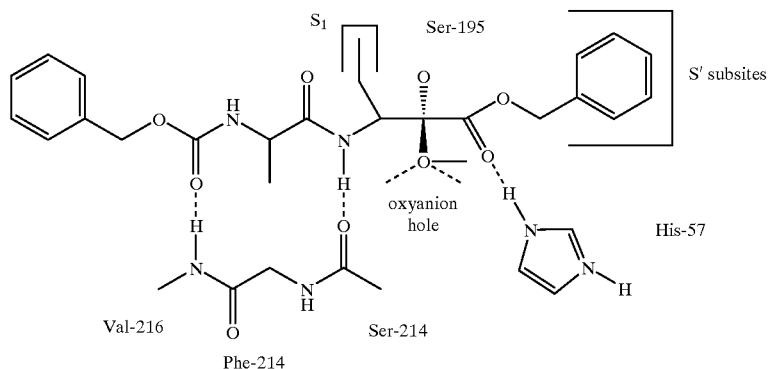

The active site of cysteine proteases share several features in common with serine proteases including an active site histidine residue. In place of the Ser-195, cysteine proteases have an active site cysteine residue which would add to the ketonic carbonyl group of the peptide keto acids, keto esters, or ketoamides to form an adduct very similar to the structure depicted above except with a cysteine residue replacing the serine-195 residue. Additional interactions would occur between the extended substrate binding site of the cysteine protease and the inhibitor which would increase the binding affinity and specificity of the inhibitors.

Inhibitor Design and Selection

The peptide and amino acid α-ketoamide derivatives, as shown in the above crystal structure, bind to the enzymes using many of the interactions that are found in complexes of a particular individual enzyme with its substrates. In order to design an inhibitor for a particular serine or cysteine protease, it is necessary to: 1) find the amino acid sequences of good peptide substrates for that enzyme, and 2) place those or similar amino acid sequences into a α-ketoamide structure. Additional interactions with the enzyme can be obtained by tailoring the R group of the inhibitor to imitate the amino acid residues which are preferred by an individual protease at the $S_1'$ and $S_2'$ subsites. For example, ketoesters with $R_3$ and/or $R_4$=branched alkyl groups would interact effectively with serine and cysteine proteases which prefer Leu, Ile, and Val residues at $P_1'$ and/or $P_2'$, while amides with R=alkyl substituted with phenyl would interact effectively with serine and cysteine proteases which prefer Phe, Tyr, Trp residues at $P_1'$ and/or $P_2'$. Likewise, the $M_1$ group can be tailored to interact with the S subsites of the enzyme. This design strategy will also work when other classes of peptide inhibitors are used in place of the peptide substrate to gain information on the appropriate sequence to place in the ketoester, ketoacid, or ketoamide inhibitor. Thus, we are able to predict the structure of new inhibitors for other serine and cysteine proteases based on knowledge of their substrate specificities. Once a good inhibitor structure for a particular enzyme is found, it is then possible to change other characteristics such as solubility or hydrophobicity by adding substituents to the $M_1$ or $R_3$ and $R_4$ groups.

Elastase is an enzyme which hydrolyzes most effectively tetra- and tripeptides having $P_1$ residues with small alkyl side chains such as Ala and Val. MeO—Suc—Ala—Ala—Ala—Val—NA and Z—Ala—Ala—Ala—Ala—NA are good substrates (NA=4-nitroanilide). Thus the corresponding α-ketoamide Z—Ala—Ala—Ala—DL—Ala—CO—$NR_3R_4$ and MeO—Suc—Ala—Ala—Pro—DL—Abu—CO—$NR_3R_4$ will be excellent elastase inhibitors. Suc—Phe—Leu—Phe—NA is an excellent substrate for chymotrypsin, cathepsin G, and mast cell chymases. Thus, the corresponding α-ketoamide will be an excellent inhibitor for these chymotrypsin-like enzymes. In the case of the cysteine protease calpain, a good inhibitor sequence is Ac—leu—Leu—Nle—H. We have found that ketoesters related in structure such as Z—Leu—Abu—CO—$NR_3R_4$ and Z—Leu—Phe—CO—$NR_3R_4$ are potent inhibitors for calpain.

The following structures are predicted to be potent inhibitors for the listed enzymes. The inhibitor sequences were obtained from peptide substrate and/or inhibitor sequences in the protease literature.

| Inhibitor | Target |
|---|---|
| Z-Gly-Leu-Phe-CO—$NR_3R_4$ | for cathepsin G and RMCP II |
| MeO-Suc-Ala-Ala-Pro-Met-CO—$NR_3R_4$ | for cathepsin G |
| Boc-Ala-Ala-Asp-CO—$NR_3R_4$ | for human lymphocyte granzyme B |
| Suc-Pro-Leu-Phe-CO—$NR_3R_4$ and Boc-Ala-Ala-Phe-CO—$NR_3R_4$ | for RMCP I (RMCP = rat mast cell protease) |
| Boc-Gly-Leu-Phe-CO—$NR_3R_4$, Suc-Phe-Leu-Phe-CO—$NR_3R_4$ | for human and dog skin chymase |
| Boc-Ala-Ala-Glu-CO—$NR_3R_4$ | for *S. aureus* V-8 protease |
| Z-Gly-Gly-Pro-CO—$NR_3R_4$ | for human prolyl endopeptidase |
| Ala-Pro-CO—$NR_3R_4$ | for DPP IV |
| Suc-Ala-Ala-Pro-Val-CO—$NR_3R_4$ | for PPE |
| Suc-Lys(Cbz)-Val-Pro-Val-CO—$NR_3R_4$, adamantyl-$SO_2$-Lys($COCH_2CH_2CO_2H$)-Ala-Val-CO—$NR_3R_4$, adamantyl-$CH_2CH_2$OCO-Glu(O-t-Bu)-Pro-Val-CO—$NR_3R_4$, and adamantyl-$SO_2$-Lys(CO—$C_6H_4CO_2H$)-Ala-Val-CO—$NR_3R_4$ | for human leukocyte (neutrophil) elastase |
| Suc-Ala-Ala-Pro-Leu-CO—$NR_3R_4$ | for elastolytic proteinase from "*Schistosoma mansoni*" |
| Glu-Phe-Lys-CO—$NR_3R_4$ and Dns-Ala-Phe-Lys-CO—$NR_3R_4$ | for plasmin |
| D-Val-Gly-Arg-CO—$NR_3R_4$ and Dns-Glu-Gly-Arg-CO—$NR_3R_4$ | for factor Xa |
| Z-Phe-Arg-CO—$NR_3R_4$ and Z-Trp-Arg-CO—$NR_3R_4$ | for porcine pancreatic and human plasma kallikreins |
| Z-Lys-Arg-CO—$NR_3R_4$ | for human skin tryptase |
| Z-Gly-Arg-CO—$NR_3R_4$ | for human lung tryptase |
| Z-Ile-Ala-Gly-Arg-CO—$NR_3R_4$ | for factors IXa, Xa, XIa, XIIa and bovine plasma kallikrein |
| Glu-Gly-Arg-CO—$NR_3R_4$ | for urokinase |
| Dns-Phe-Pro-Arg-CO—$NR_3R_4$ | for plasminogen activator |
| Dns-Ile-Pro-Arg-CO—$NR_3R_4$ | for activated protein C |
| Z-Trp-Arg-CO—$NR_3R_4$ | for bovine factor IXa |
| Z-Gly-Arg-CO—$NR_3R_4$ | for bovine factor Xa and XIa |
| Z-Phe-Arg-CO—$NR_3R_4$ | for bovine factor XIIa |
| Dns-Glu-Gly-Arg-CO—$NR_3R_4$ | for human factor Xa |
| D-Phe-Pro-Arg-CO—$NR_3R_4$, D-MePhe-Pro-Arg-CO—$NR_3R_4$, and Boc-D-Phe-Pro-Arg-CO—$NR_3R_4$ | for human thrombin |
| Z-Phe-Gly-Arg-CO—$NR_3R_4$ | for trypsin |
| Cl—$C_6H_4CH_2$OCO-Phe-Gly-CO—$NR_3R_4$ | for papain |
| $C_6H_5CH_2$NHCO-Gly-Phe-Gly-CO—$NR_3R_4$ | for cathepsin B |

$R_3$ and $R_4$ are selected independently from the group consisting of H, $C_{1-20}$ alkyl, $C_{3-20}$ cyclized alkyl, $C_{1-20}$ alkyl with a phenyl group attached to the $C_{1-20}$ alkyl, $C_{3-20}$ cyclized alkyl with an attached phenyl group, $C_{1-20}$ alkyl with an attached phenyl group substituted with K, $C_{1-20}$ alkyl with an attached phenyl group disubstituted with K, $C_{1-20}$ alkyl with an attached phenyl group trisubstituted with K, $C_{3-20}$ cyclized alkyl with an attached phenyl group substituted with K, $C_{1-10}$ alkyl with a morpholine [—N($CH_2CH_2$)O] ring attached through nitrogen to the alkyl, $C_{1-10}$ alkyl with a piperidine ring attached through nitrogen to the alkyl, $C_{1-10}$ alkyl with a pyrrolidine ring attached through nitrogen to the alkyl, $C_{1-20}$ alkyl with an OH group attached to the alkyl, —$CH_2CH_2OCH_2CH_2$OH, $C_{1-10}$ with an attached 4-pyridyl group, $C_{1-10}$ with an attached 3-pyridyl group, $C_{1-10}$ with an attached 2-pyridyl group, $C_{1-10}$ with an attached cyclohexyl group, —NH—$CH_2CH_2$—(4-hydroxyphenyl), and —NH—$CH_2CH_2$-(3-indolyl).

In Vitro Uses

To use the above inhibitors in vitro, they are dissolved in an organic solvent such as dimethylsulfoxide or ethanol, and are added to an aqueous solution containing serine and/or cysteine proteases. The fmal concentration of the organic solvent should be less than 25%. The inhibitors may also be added as solids or in suspension. The serine and cysteine protease inhibitors of this invention would be useful in a variety of experimental procedures where proteolysis is a significant problem. Inclusion of these inhibitors in a radio-immunoassay experiments would result in higher sensitivity. The use of these inhibitors in plasma fractionation procedures would result in higher yields of valuable plasma proteins and would make purification of the proteins easier. The inhibitors disclosed here could be used in cloning experiments utilizing bacterial cultures, yeast and human cells to yield a purified cloned product in higher yield.

The novel compounds of this invention are effective in the prevention of unnecessary proteolysis caused by chymotrypsin-like and elastase-like enzymes in the process of purification, transport and storage of peptides and proteins as shown in Table II by effective inhibition of chymotrypsin and elastase and other cysteine proteases.

In Vivo Uses

Effective inhibitors of the proteolytic function of human leukocyte elastase and chymotrypsin-like enzymes (Table II) would have anti-inflammatory activity and can be used to treat and control emphysema, adult respiratory distress syndrome and rheumatoid arthritis. Effective inhibitors of the proteolytic function of chymotrypsin and pancreatic elastase (Table II) are effective for theraputic use in the treatment of pancreatitis.

Peptide α-ketoamide can be used to control protein turnover, muscular dystrophy, myocardial tissue damage, tumor metastasis, and bone resorption as shown in Table I by effective inhibition of lysosomal cathepsin B in buffer. Peptide α-ketoamides can also be used as neuroprotectants or for the treatment of ischemia, stroke or Alzheimer's disease as shown in Table I by effective inhibiton of calpain I and calpain II.

Considerable evidence has shown that leukocyte elastase and/or related enzymes play a role in tumor cell metastasis [Salo et al., *Int. J. Cancer* 30, pp 669–673 (1973); Kao et al., *Biochem. Biophys. Res. Comm.* 105, pp 383–389 (1982); Powers, J. C. in Modification of Proteins, R. E. Feeney and J. R. Whitaker, eds., Adv. Chem. Ser 198, Amer. Chem. Soc., Wash., D. C. pp 347–367 (1982); all incorporated herein by reference], therefore it is suggested that compounds of this invention may have anti-tumor activity.

Pulmonary emphysema is a disease characterized by progressive loss of lung elasticity due to the destruction of lung elastin and alveoli. The destructive changes of lung parentchyma associated with pulmonary emphysema are caused by uncontrolled proteolysis in lung tissues [Janoff, Chest 83, 54–58 (1983); incorporated herein by reference]. A number of proteases have been shown to induce emphysema in animals [Marco et al., *Am. Rev. Respir. Dis.* 104, 595–598 (1971); Kaplan, *J. Lab. Clin. Med.* 82, 349–356 (1973); incorporated herein by reference], particularly human leukocyte elastase [Janoff, ibid 115, 461–478 (1977); incorporated herein by reference]. Leukocyte elastase and other mediators of inflammation also appear to play a role in diseases such as mucocutaneous lymph node syndrome [Reiger et al., *Eur. J. Pediatr.* 140, 92–97 (1983); incorporated herein by reference] and adult respiratory distress syndrome [Stockley, *Clinical Science* 64, 119–126 (1983); Lee et al., *N. Eng. J. Med.* 304, 192–196 (1981); Rinaldo, ibid 301, 900–909 (1982); incorporated herein by reference].

It is known that in vitro activity of elastase inhibitors correlates with in vivo activity in animal models of emphysema and inflammation [Otterness et al., editors, Advances in Inflammation Research, Vol. 11, Raven Press 1986; incorporated herein by reference]. Prophylactic administration of an inhibitor of elastase significantly diminishes the extent of elastase-induced emphysema [Kleinerman et al., *Am. Rev. Resir. Dis.* 121, 381–387 (1980); Lucey et al., *Eur. Respir. J.* 2, 421–427 (1989); incorporated herein by reference]. Thus the novel inhibitors described here should be usefull for the treatment of emphysema and inflammation. Elastase inhibitors have been used orally, by injection, or by instillation in the lungs in animal studies (Powers, *Am. Rev. Respir. Dis.*, 127, s54–s58 (1983); Powers and Bengali, *Am. Rev. Respir. Dis.* 134, 1097–1100 (1986); these two articles are incorporated herein by reference). The inhibitors described above can be used by any of these routes.

Drug Delivery

For therapeutic use, the peptide α-ketoamides may be administered orally, topically or parenterally. The term parenteral as used includes subcutaneous injection, intravenous, intramuscular, intrasternal injection or infusion techniques. The dosage depends primarily on the specific formulation and on the object of the therapy or prophylaxis. The amount of the individual doses as well as the administration is best determined by individually assessing the particular case.

The pharmaceutical compositions containing the active ingredient may be in a form suitable for oral use, for example as tablets, troches, lozenges, aqueous or oily suspensions, dispersible powders or granules, emulsions, hard or soft capsules or syrups or elixirs. Dosage levels of the order to 0.2 mg to 140 mg per kilogram of body weight per day are useful in the treatment of above-indicated conditions (10 mg to 7 gms per patient per day). The amount of active ingredient that may be combined with carrier materials to produce a single dosage form will vary depending upon the host treated and the particular mode of administration.

For injection, the therapeutic amount of the peptide α-ketoamides or their pharmaceutically acceptable salts will normally be in the dosage range from 0.2 to 140 mg/kg of body weight. Administration is made by intravenous, intramuscular or subscutaneous injection. Accordingly, pharmaceutical compositions for parenteral administration will contain in a single dosage form about 10 mg to 7 gms of the compounds per dose. In addition to the active ingredient, these pharmaceutical compositions will usually contain a buffer, e.g. a phosphate buffer which keeps the pH in the range from 3.5 to 7 and also sodium chloride, mannitol or sorbitol for adjusting the isotonic pressure.

A composition for topical application can be formulated as an aqueous solution, lotion, jelly or an oily solution or suspention. A composition in the form of an aqueous solution is obtained by dissolving the compounds of this invention in aqueous buffer solution of pH 4 to 6.5 and if desired, adding a polymeric binder. An oily formulation for topical application is obtained by suspending the compounds of this invention in an oil, optionally with the addition of a swelling agent such as aluminium stearate and/or a surfactant.

SYNTHETIC METHODS

The α-ketoamide inhibitors are prepared from the corresponding α-ketoamide. The ketoester inhibitors are prepared by a two step Dakin-West from the corresponding peptide acid (Charles et al., J. Chem. Soc. Perkin 1, 1139–1146, 1980). This procedure can be utilized with either amino acid derivatives, dipeptide derivatives, tripeptide derivatives, or tetrapeptide derivatives as shown in the following scheme.

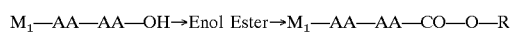

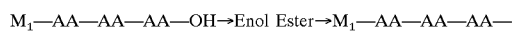

AA—CO—O—R $M_1$—AA—AA—AA—AA—OH→Enol Ester→$M_1$—AA—AA—AA—AA—CO—O—R

The precursor peptide can be prepared using standard peptide chemistry which is well described in publications such as *The Peptides, Analysis, Synthesis, Biology*, Vol. 1–9, published in 1979–1987 by Academic Press and Houben-Weyl Methoden der Organischen Chemie, Vol. 15, Parts 1 and 2, *Synthese von Peptiden*, published by Georg Thieme Verlag, Stuttgart in 1974 (both references incorporated herein by reference).

The $M_1$ group can be introduced using a number of different reaction schemes. First it could be introduced directly on an amino acid as shown in the following scheme (top), or the $M_1$ group could be introduced by reaction with an amino acid ester, followed by removal of the ester group to give the same product (bottom).

H—AA—OH→$M_1$—AA—OH

H—AA—OR'→$M_1$—AA—OR'→$M_1$—AA—OH

The techniques for introduction of the $M_1$ group is well documented in the The Peptides, Houben-Weyel, and many other textbooks on organic synthesis. For example reaction with cyanate orpnitrophenyl cyanate would introduce a carbamyl group ($M_1$=$NH_2CO$—). Reaction with $Me_2NCOCl$ would introduce the $Me_2NCO$— group. Reaction with p-nitrophenyl thiocarbamate would introduce a thio carbamyl group ($M_1$=$NH_2CS$—). Reaction with $NH_2SO_2Cl$ would introduce the $NH_2SO_2$— group. Reaction with $Me_2NSO_2Cl$ would introduce the $Me_2NSO_2$— group. Reaction with a substituted alkyl or aryl isocyanate would introduce the X—NH—CO— group where X is a substituted alkyl or aryl group. Reaction with a substituted alkyl or aryl isothiocyanate would introduce the X—NH—CS— group where X is a substututed alkyl or aryl group. Reaction with X—$SO_2$—Cl would introduce the X—$SO_2$— group. Reaction with a substituted alkyl or aryl acid chloride would introduce an acyl group (M=X—CO—). For example, reaction with MeO—CO—$CH_2CH_2$—CO—Cl would give the X—CO— group where X is a $C_2$ alkyl substituted with a $C_1$ alkyl—OCO— group. Reaction with a substituted alkyl or aryl thioacid chloride would introduce a thioacyl group (M=X—CS—). Reaction with an a substituted alkyl or aryl sulfonyl chloride would introduce an X—$SO_2$— group. For example reaction with dansyl chloride would give the X—$SO_2$— derivative where X was a naphthyl group mono substituted with a dimethylamino group. Reaction with a substituted alkyl or aryl chloroformate would introduce a X—O—CO— group. Reaction with a substituted alkyl or aryl chlorothioformate would introduce a X—O—CS—. There are many alternate reaction schemes which could be used to introduce all of the above $M_1$ groups to give either $M_1$—AA—OH or $M_1$—AA—OR'.

The $M_1$—AA—OH derivatives could then be used directly in the Dakin-West reaction or could be converted into the dipeptides, tripeptides, and tetrapeptides $M_1$—AA—AA—OH, $M_1$—AA—AA—AA—OH, or $M_1$—AA—AA—AA—AA—OH which could be be used in the Dakin-West reaction. The substituted peptides $M_1$—AA—AA—OH, $M_1$—AA—AA—AA—OH, or $M_1$—AA—AA—AA—AA—OH could also be prepared directly from H—AA—AA—OH, H—AA—AA—AA—OH, or H—AA—AA—AA—AA—OH using the reactions described above for introduction of the $M_1$ group. Alternately, the $M_1$ group could be introduced by reaction with carboxyl blocked peptides to give $M_1$—AA—AA—OR', $M_1$—AA—AA—AA—OR', or $M_1$—AA—AA—AA—AA—OR', followed by the removal of the blocking group R'.

The R group in the ketoester structures is introduced during the Dakin-West reaction by reaction with an oxalyl chloride Cl—CO—CO—O—R. For example, reaction of $M_1$—AA—AA—OH with ethyl oxalyl chloride Cl—CO—CO—O—Et gives the keto ester $M_1$—AA—AA—CO—O—Et. Reaction of $M_1$—AA—AA—AA—AA—OH with Cl—CO—CO—O—Bzl would give the ketoester $M_1$—AA—AA—AA—AA—CO—O—Bzl. Clearly a wide variety of R groups can be introduced into the ketoester structure by reaction with various alkyl or arylalkyl oxalyl chlorides (Cl—CO—CO—O—R). The oxalyl chlorides are easily prepared by reaction of an alkyl or arylalkyl alcohol with oxalyl chloride Cl—CO—CO—Cl. For example, Bzl—O—CO—CO—Cl and n-Bu—CO—CO—Cl are prepared by reaction of respectively benzyl alcohol and butanol with oxalyl chloride in yields of 50% and 80% [Warren, C. B., and Malee, E. J., *J. Chromatography* 64, 219–222 (1972); incorporated herein by reference].

Ketoamides $M_1$—AA—CO—$NR_3R_4$, M—AA—AA—CO—$NR_3R_4$, M—AA—AA—AA—CO—$NR_3R_4$, M—AA—AA—AA—AA—CO—$NR_3R_4$ were prepared indirectly from the ketoesters. The ketone carbonyl group was first protected as shown in the following scheme and then the ketoamide was prepared by reaction with an amine H-$NR_3R_4$. The illustrated procedure should also work with other protecting groups. In addition, the corresponding ketoacid could be used as a precursor. Blocking the ketone carbonyl group of the ketoacid and then coupling with an amine H—$NR_3R_4$ using standard peptide coupling reagents would yield an intermediate which could then be deblocked to form the ketoamide.

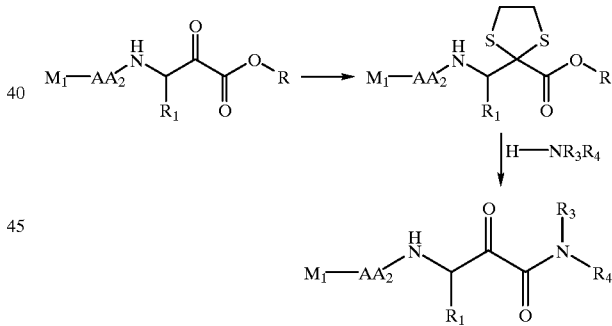

Most of the aspartyl α-keto amides (12–15, 24–36) were synthesized by an adaption of the strategy of Wasserman et aL (Scheme 1 and 2) [Wasserman, H. H. and Ho, W.-B., *J. Org. Chem.* 59, 4364–4366(1994) incorporated herein by reference]. The mixed anhydride of a protected Laspartic acid derivative (2–4) was added to the cyanophosphorane generated in situ from the corresponding phosphonium bromide (1) [Hamper, B. C., *J. Org. Chem.* 53, 5558–5562 (1988) incorporated herein by reference]. The aspartylphosphorane (5–7) was then ozonolyzed at −78° C. and the highly reactive dicarbonylnitrile intermediate was treated with the appropriate amine to generate the α-keto amide (8–11). Removal of the benzyl ester by hydrogenation in the presence of Pearlmann's catalyst or by stirring the α-keto amide in trifluoroacetic acid gave the aspartyl α-keto amide inhibitors 12–14 and 15 respectively. Alternatively, the Boc group was removed using HCl gas in ethyl acetate (Scheme 2) and the deprotected amines (22, 23) were either hydrogenated to give the unprotected aspartyl α-keto amides (24, 25) or coupled with a variety of acids, followed by hydrogenation to give the required inhibitors (26–36).

Scheme 1

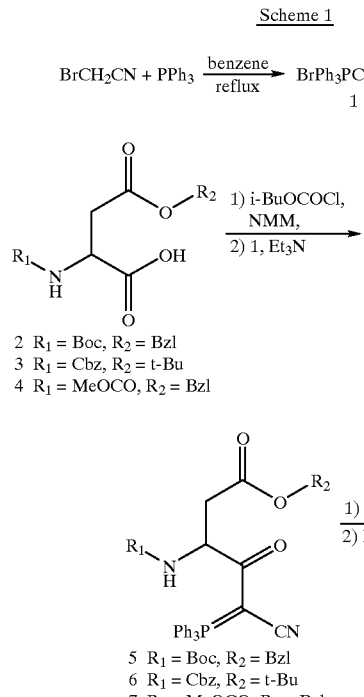

2  $R_1$ = Boc, $R_2$ = Bzl
3  $R_1$ = Cbz, $R_2$ = t-Bu
4  $R_1$ = MeOCO, $R_2$ = Bzl

5  $R_1$ = Boc, $R_2$ = Bzl
6  $R_1$ = Cbz, $R_2$ = t-Bu
7  $R_1$ = MeOCO, $R_2$ = Bzl

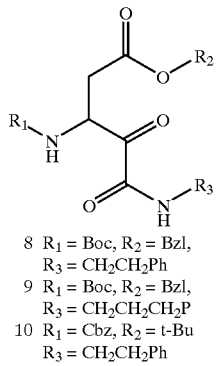

8  $R_1$ = Boc, $R_2$ = Bzl, $R_3$ = CH$_2$CH$_2$Ph
9  $R_1$ = Boc, $R_2$ = Bzl, $R_3$ = CH$_2$CH$_2$CH$_2$P
10 $R_1$ = Cbz, $R_2$ = t-Bu, $R_3$ = CH$_2$CH$_2$Ph

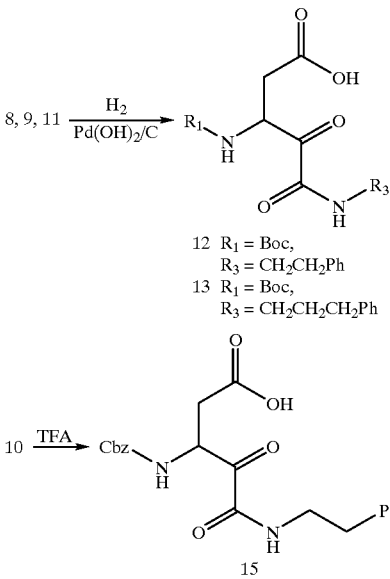

12 $R_1$ = Boc, $R_3$ = CH$_2$CH$_2$Ph
13 $R_1$ = Boc, $R_3$ = CH$_2$CH$_2$CH$_2$Ph

15

Scheme 2

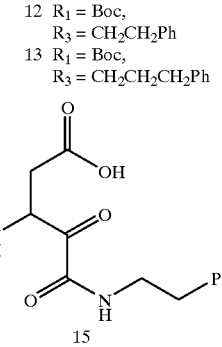

22 $R_3$ = CH$_2$CH$_2$Ph
23 $R_3$ = CH$_2$CH$_2$CH$_2$Ph

24 $R_3$ = CH$_2$CH$_2$Ph
25 $R_3$ = CH$_2$CH$_2$CH$_2$Ph

1) $R_4$—OH, NMM, i-BuOCOCl
2) H$_2$, Pd(OH)$_2$/C

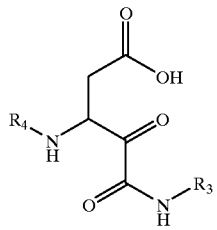

26 $R_3$ = $CH_2CH_2Ph$, $R_4$ = $PhCH_2SO_2$
27 $R_3$ = $CH_2CH_2Ph$, $R_4$ = $(CH_3)_2CH_2CO$-Gly
28 $R_3$ = $CH_2CH_2Ph$, $R_4$ = $PhCH_2CH_2CO$-Ala-Ala
29 $R_3$ = $CH_2CH_2Ph$, $R_4$ = $PhCH_2CH_2CO$-Val-Gly
31 $R_3$ = $CH_2CH_2Ph$, $R_4$ = $PhCH_2CH_2CO$-Val-Ala
33 $R_3$ = $CH_2CH_2Ph$, $R_4$ = p-Cl—$PhCH_2CH_2CO$-Val-Ala
35 $R_3$ = $CH_2CH_2Ph$, $R_4$ = Ac-Tyr-Val-Ala
36 $R_3$ = $CH_2CH_2CH_2Ph$, $R_4$ = Ac-Tyr-Val-Ala

Four of the peptidyl α-keto amides (54–57) were prepared by an alternative method (Scheme 3) [Gmeiner, P., Junge, D. & Kartner, A. *J. Org. Chem.* 59, 6766–6776 (1994) by reference]. Aspartic acid was benzylated to give (37) followed by reduction to the diol derivative 38. The C-4 alcohol was selectively protected as the dimethyl t-butylsilyl ether (39) and the C-1 alcohol was oxidized to the aldehyde (40). After stirring in neat trimethylsilylcyanide, the cyanohydrin (41) was hydrolyzed and the crude intermediate was coupled to the appropriate amine to give a dihydroxy amide (42, 43). After debenzylation in the presence of Pearlmann's catalyst, the dihydroxyamine (44,

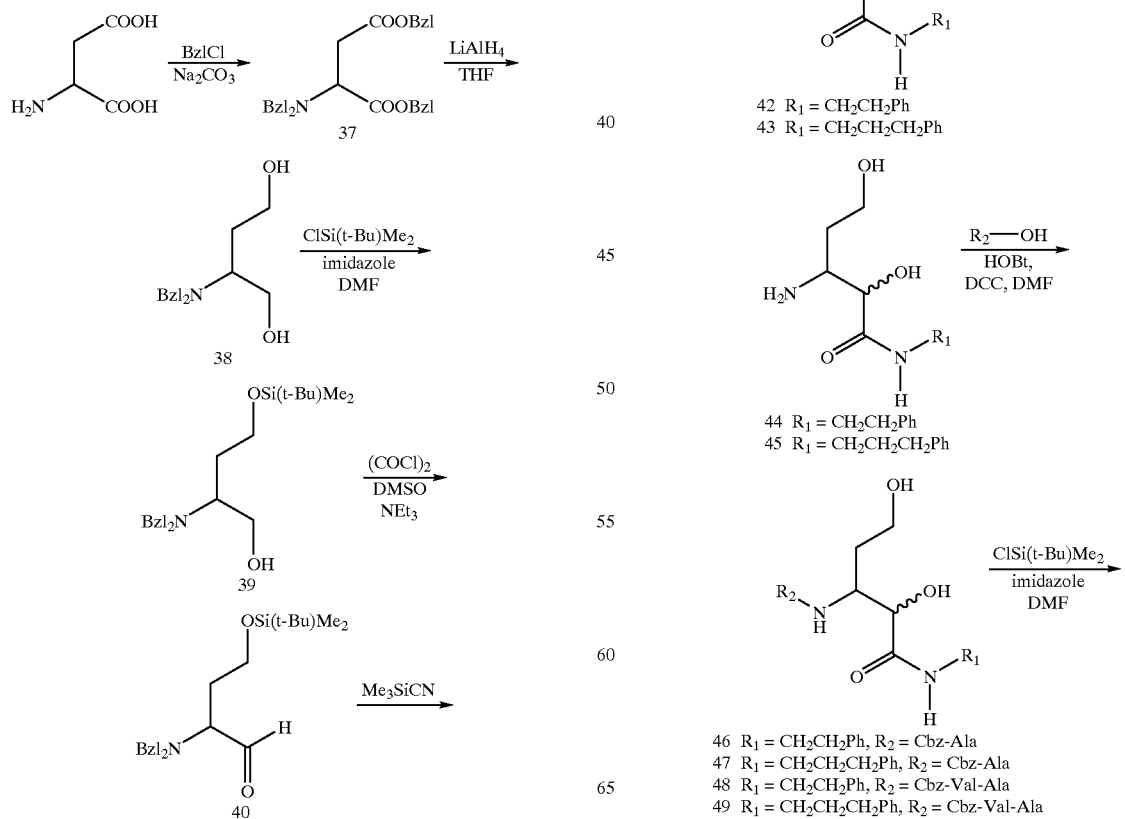

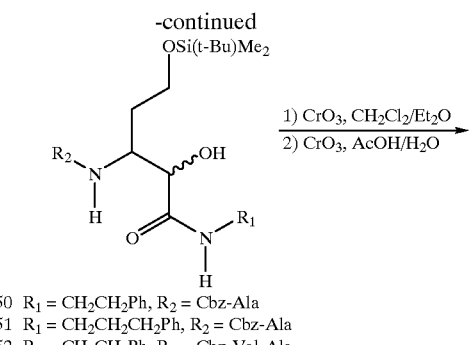

50 R₁ = CH₂CH₂Ph, R₂ = Cbz-Ala
51 R₁ = CH₂CH₂CH₂Ph, R₂ = Cbz-Ala
52 R₁ = CH₂CH₂Ph, R₂ = Cbz-Val-Ala
53 R₁ = CH₂CH₂CH₂Ph, R₂ = Cbz-Val-Ala

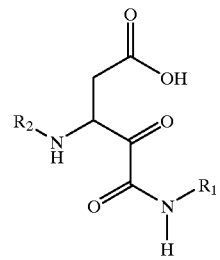

54 R₁ = CH₂CH₂Ph, R₂ = Cbz-Ala
55 R₁ = CH₂CH₂CH₂Ph, R₂ = Cbz-Ala
56 R₁ = CH₂CH₂Ph, R₂ = Cbz-Val-Ala
57 R₁ = CH₂CH₂CH₂Ph, R₂ = Cbz-Val-Ala 45) was coupled with the required acid to give the corresponding peptidyl dihydroxy amide (46–49). Several attempts at directly oxidizing the dihydroxy amide to the final α-keto amide product were not successful. Mild to strong basic oxidation conditions produced mostly the starting diol, byproducts such as the dehydrated aldehyde or cyclized lactone, mixed with the desired α-keto amide. Under mild acidic oxidation conditions (chromic acid), the starting diol and the lactone were obtained. Under strong acidic oxidation conditions (Jones reagent) only decomposed products were obtained. Thus, it was necessary to oxidize the primary and secondary alcohols separately. Therefore, the primary alcohol was protected again (50–53) and the final form of the α-keto amide was obtained by a consecutive double oxidation where the silyl protecting group was simultaneously removed at the second oxidation stage with chromic acid in acetic acid.

The peptide acids (R₄—OH in Scheme 2 and R₂—OH in Scheme 3) were prepared for the most part by standard peptide coupling methods.

The following detailed examples are given to illustrate the invention and are not intended to limit it in any manner.

EXAMPLE 1

Z—Leu—Phe—CONH—Et

To a stirred solution of Z—Leu—Phe—OH (20 g, 48.5 mmole), 4-dimethylaminopyridine (0.587 g, 4.8 mmole), and pyridine (15.7 ml, 194 mmole) in anhydrous THF (100 ml) was added ethyl oxalyl chloride (11.4 ml, 101.8 mmole) at a rate sufficient to initiate refluxing. The mixture was gently refluxed for 4 hours, cooled to room temperature, and water (80 ml) was added. The reaction mixture was stirred vigorously for 30 min, and extracted with ethyl acetate (3×100 ml). The combined organic layers were washed with water (2×100 ml), saturated sodium chloride (2×100 ml), decolorized with decolorizing carbon, dried over magnesium sulfate, and concentrated, leaving a dark orange oil. Chromatography on a silica gel column with CHCl₃/CH₃OH (50:1 v/v) afforded 14.63 g (y=53%) of Z—Leu—Phe—enolester. The product was a yellow oil. Single spot on TLC, $R_f$=0.77 (CHCL₃/CH₃OH 50:1). NMR (CDCl₃) ok.

To a stirred pale yellow solution of the Z—Leu—Phe—enolester (14.63 g, 25.73 mmole) in anhydrous ethanol (50 ml) was added a solution of sodium ethoxide (0.177 g, 2.6 mmole) in ethanol (5 ml). The orange solution was stirred for 3 hours at room temperature, then the ethanol was evaporated and the residue was treated with ethyl ether (300 ml). The ether layer was washed with water (2×100 ml), saturated sodium chloride (2'100 ml), dried over magnesium sulfate, and concentrated, leaving a orange oil. Chromatography on a silica gel column with CHCl₃/CH₃OH (50:1 v/v) afforded 7.76 g (y=64%) of the α-ketoester Z—Leu—Phe—COOEt. The product was a yellow oil. Single spot on TLC, $R_f$=0.44 (CHCl₃/CH₃OH 50:1). NMR (CDCl₃) ok. MS (FAB, calcd. for C₂₆H₃₂N₂O₆:468.6), m/e=469 (M+1).

The α-carbonyl group of Z—Leu—Phe—COOEt was protected by the following procedure. To a solution of Z—Leu—Phe—COOEt (1 g, 2.13 mmole) in 5 ml of CH₂Cl₂ was added 1,2-ethanedithiol (0.214 ml, 2.55 mmole), followed by 0.5 ml of boron trifluoride etherate. The solution was stirred overnight at room temperature. Water (20 ml) and ethyl ether (20 ml) were added. The organic layer was separated, washed with water (2×10 ml), saturated sodium chloride (2×10 ml), dried over magnesium sulfate, and evaporated to afford 0.98 g (y=84%) yellow semisolid.

The protected α-ketoester (0.98 g, 1.8 rnmole) was dissolved in ethanol (5 ml), cooled tc 0–5° C. in an ice bath, and ethylamine was bubbled through the solution until 2.43 g (54 mmole) had been added. The reaction mixture was allowed to warm to room temperature slowly, and stirred overnight. The mixture was filtered, a white precipitate was removed, leaving a yellow semisolid. Chromatography on a silica gel column with CHCl₃/CH₃OH (30:1 v/v) afford 0.63 g (y=75%) of Z—Leu—Phe—CONH—Et. The product was a pale yellow solid. Single spot on TLC, $R_f$=0.60 (CHCl₃/CH₃OH 20:1); mp 145–147° C. Anal. calcd. for C₂₆H₃₃N₃O₅:467.56; C, 66.79; H, 7.11; N,8.99; found: C, 66.59; H, 7.09; N, 8.95. NMR (CDCl₃) ok. MS (FAB) m/e=468 (M+1).

EXAMPLE 2

Z—Leu—Phe—CONH—nPr

This compound was synthesized from the protected α-ketoester and propylamine in 92% yield by the procedure described in Example 1. Single spot on TLC, $R_f$=0.50 (CHCl₃/CH₃OH 50:1); mp 152–153° C. Anal. calcd. for C₂₇H₃₅N₃O₅:481.57; C, 67.33; H, 7.33; N, 8.72. Found: C, 67.21; H, 7.38; N, 8.64. NMR (CDCl₃) ok. MS (FAB) m/e=482 (M+1).

EXAMPLE 3

Z—Leu—Phe—CONH—nBu

This compound was synthesized from the protected α-ketoester and butylamine in 67% yield by the procedure described in Example 1. Single spot on TLC, $R_f$=0.50. (CHCl₃/CH₃OH 50:1); mp 152–153° C. Anal. calcd. for C₂₈H₃₇N₃O₅:495.59; C, 67.85; H, 7.52; N, 8.48. Found: C, 67.70; H, 7.57; N, 8.43. NMR (CDCl₃) ok. MS (FAB) m/e=496 (M+1).

EXAMPLE 4

Z—Leu—Phe—CONH—iBu

This compound was synthesized from the protected α-ketoester and isobutylamine in 53% yield by the procedure described in Example 1. Single spot on TLC, $R_f$=0.54 (CHCl$_3$/CH$_3$OH 50:1); mp 152° C. Anal. calcd. for C$_{28}$H$_{37}$N$_3$O$_5$:495.59; C, 67.85; H, 7.52; N, 8.48. Found: C, 67.77; H, 7.56; N, 8.40. NMR (CDCl$_3$) ok. MS (FAB) m/e=496 (M+1).

EXAMPLE 5

Z—Leu—Phe—CONH—Bzl

This compound was synthesized from the protected α-ketoester and benzylamine in 40% yield by the procedure described in Example 1. After reacting overnight, ethyl acetate (60 ml) was added. The mixture was filtered to remove a white precipitate. The solution was washed with cooled 1 N HCl (3×25 ml), water (1×20 ml), saturated sodium chloride (2×20 ml), and dried over magnesium sulfate. The solution was evaporated leaving a yellow solid. Chromatography on a silica gel column with CHCl$_3$/CH$_3$OH 30:1 v/v) afforded a yellow solid. Single spot on TLC, $R_f$=0.45 (CHCl$_3$/CH$_3$OH 30:1); mp 160–162° C. Anal. calcd. for C$_{31}$H$_{35}$N$_3$O$_5$:529.61; C, 70.30; H, 6.66; N, 7.93. Found: C, 70.18; H, 6.67; N, 7.99. NMR (CDCl$_3$) ok. MS (FAB) m/e=530 (M+1).

EXAMPLE 6

Z—Leu—Phe—CONH—(CH$_2$)$_2$Ph

This compound was synthesized from the protected α-ketoester and phenethylamine in 50% yield by the procedure described in Example 5. Single spot on TLC, $R_f$=0.50 (CHCl$_3$/CH$_3$OH 30:1); mp 151–153° C. Anal. calcd. for C$_{32}$H$_{37}$N$_3$O$_5$:543.66; C, 70.70; H, 6.86; N, 7.73. Found: C, 70.54; H, 6.88; N, 7.74. NMR (CDCl$_3$) ok. MS (FAB) m/e=544 (M+1).

EXAMPLE 7

Z—Leu—Abu—CONH—Et

This compound was synthesized from protected α-ketoester derived from Z—Leu—Abu—CO$_2$Et and ethylamine in 64% yield by the procedure described in Example 1. Single spot on TlC, $R_f$=0.36 (CHCl$_3$/CH$_3$OH 50;1); mp 130–132° C. Anal. calcd. for C$_{21}$H$_{31}$N$_3$O$_5$:405.45; C, 62.20; H, 7.71; N, 10.36. Found: C, 61.92; H, 7.62; N, 10.31. NMR (CDCl$_3$) ok. MS (FAB) m/e=406 (M+1).

EXAMPLE 8

Z—Leu—Abu—CONH—nPr

This compound was synthesized from the corresponding protected α-ketoester and propylamine in 47% yield by the procedure described in Example 1. Single spot on TLC, $R_f$=0.28 (CHCl$_3$/CH$_3$OH 50:1); mp 134–135° C. Anal. calcd. for C$_{22}$H$_{33}$N$_3$O$_5$:419.50; C, 62.98; H, 7.93; N, 10.02. Found: C, 62.84; H, 7.97; N, 9.94. NMR (CDCl$_3$) ok. MS (FAB) m/e=420 (M+1).

EXAMPLE 9

Z—Leu—Abu—CONH—nBu

This compound was synthesized from the corresponding protected α-ketoester and butylamine in 42% yield by the procedure described in Example 1. Single spot on TLC, $R_f$=0.54 (CHCl$_3$/CH$_3$OH 50:1); mp 135–136° C. Anal. calcd. for C$_{23}$H$_{35}$N$_3$O$_5$:433.53; C, 63.71; H, 8.13; N, 9.69. Found: C, 63.48; H, 8.07; N, 9.67. NMR (CDCl$_3$) ok. MS (FAB) m/e=434 (M+1).

EXAMPLE 10

Z—Leu—Abu—CONH—iBu

This compound was synthesized from the conesponding protected α-ketoester and isobutylamine in 65% yield by the procedure described in Example 1. Single spot on TLC, $R_f$=0.25 (CHCl$_3$/CH$_3$OH 50:1); mp 133–135° C. Anal. calcd. for C$_{23}$H$_{35}$N$_3$O$_5$:433.52; C, 63.72; H, 8.14; N, 9.69. Found: C, 63.46; H, 8.10; N, 9.60. NMR (CDCl$_3$) ok. MS (FAB) m/e=434 (M+1).

EXAMPLE 11

Z—Leu—Abu—CONH—Bzl

This compound was synthesized from the corresponding protected α-ketoester and benzylamine in 29% yield by the procedure described in Example 5. Single spot on TLC, $R_f$=0.56 (CHCl$_3$/CH$_3$OH 30:1); mp 140–141° C. Anal. calcd. for C$_{26}$H$_{33}$N$_3$O$_5$:467.54; C, 66.79; H, 7.11; N, 8.99. Found: C, 66.65; H, 7.07; N, 8.93. NMR (CDCl$_3$) ok. MS (FAB) m/e=468 (M+1).

EXAMPLE 12

Z—Leu—Abu—CONH—(CH$_2$)$_2$Ph

This compound was synthesized from the corresponding protected α-ketoester and phenethylamine in 51% yield by the procedure described in Example 5. Single spot on TLC, $R_f$=0.44 (CHCl$_3$/CH$_3$OH30:1); mp 156–157° C. Anal. calcd. for C$_{27}$H$_{35}$N$_3$O$_5$:481.59; C, 67.34; H, 7.33; N, 8.72. Found: C, 67.38; H, 7.33; N, 8.78. NMR (CDCl$_3$) ok. MS (FAB) m/e =482 (M+1).

EXAMPLE 13

Z—Leu—Abu—CONH—(CH$_2$)$_3$—N(CH$_2$CH$_2$)$_2$O

This compound was synthesized from protected α-ketoester and 4(3-aminopropyl)morpholine in 33% yield by the procedure described in Example 1. After reacting overnight, ethyl acetate (80 ml) was added. The mixture was filtered to remove a white precipitate. The solution was washed with water (3×20 ml), saturated sodium chloride (2×20 ml), and dried over magnesium sulfate. The solution was evaporated leaving a yellow oil. Chromatography on a silica gel column with CHCl$_3$/CH$_3$OH (10:1 v/v) afforded a yellow semisolid, which was recrystallized from ethyl acetatelhexane to obtain a pale yellow solid. Single spot on TLC, $R_f$=0.42 (CHCl$_3$/CH$_3$OH 10:1); mp 125–126° C. Anal. calcd. for C$_{26}$H$_4$N$_4$O$_6$:504.63; C, 61.88; H, 7.99; N, 11.10. Found: C, 61,69; H, 7.95; N, 11.07. NMR (CDCl$_3$) ok. MS (FAB) m/e=505 (M+1).

EXAMPLE 14

Z—Leu—Abu—CONH—(CH$_2$)$_7$CH$_3$

This compound was synthesized from the corresponding protected α-ketoester and octylamine in 67% yield by the procedure described in Example 5. It was white solid. Single spot on TLC, $R_f$=0.55 (CHCl$_3$/CH$_3$OH 30:1); mp 134–135° C. Anal. calcd. for C$_{27}$H$_{43}$N$_3$O$_5$: 489.66; C, 66.23; H, 8.85; N, 8.58. Found: C, 66.19; H, 8.81; N, 8.61. NMR (CDCl$_3$) ok. MS (FAB) m/e=490 (M+1).

EXAMPLE 15

Z—Leu—Abu—CONH—(CH$_2$)$_2$OH

This compound was synthesized from the corresponding protected α-ketoester and ethanolamine in 29% yield by the procedure described in Example 13. The product was a white sticky solid. Single spot on TLC, $R_f$=0.42 (CHCl$_3$/CH$_3$OH 10:1); mp 151–153° C. Anal: calcd. for $C_{21}H_{31}N_3O_6$:421.49; C, 59.84; H, 7.41; N, 9.97. Found: C, 59.11; H, 7.44; N, 9.81. NMR (CDCl$_3$) ok. MS (FAB) m/e=422 (M+1).

EXAMPLE 16

Z—Leu—Abu—CONH—(CH$_2$)$_2$O(CH$_2$)$_2$OH

This compound was synthesized from the corresponding protected α-ketoester and 2-(2-aminoethoxy)ethanol in 34% yield by the procedure described in Example 13. The product was white sticky solid. Single spot on TLC, $R_f$=0.42 (CHCl$_3$/CH$_3$OH 10:1); mp 103–105° C. Anal.: calcd. for $C_{23}H_{35}N_3O_7$: 465.55; C, 59.34; H, 7.58; N, 9.03. Found: C, 59.23; H, 7.58; N, 9.01. NMR (CDCl$_3$) ok. MS (FAB) m/e=466 (M+1).

EXAMPLE 17

Z—Leu—Abu—CONH—(CH$_2$)$_{17}$CH$_3$

This compound was synthesized from the corresponding protected α-ketoester and octadecylamine in 12% yield by the procedure described in Example 5. The product was a pale yellow solid. Single spot on TLC, $R_f$=0.54 (CHCl$_3$/CH$_3$OH 30:1); mp 134–136° C. Anal: calcd. for $C_{37}H_{63}N_3O_5$:629.92; C, 70.55; H, 10.08; N, 6.67. Found: C, 70.71; H, 10.14; N, 6.75. NMR (CDCl$_3$) ok. MS (FAB) m/e=630.2 (M+1).

EXAMPLE 18

Z—Leu—Abu—CONH—CH$_2$—C$_6$H$_3$(OCH$_3$)$_2$

This compound was synthesized from the corresponding protected α-ketoester and 3,5-dimethoxybenzylamine in 45% yield by the procedure described in Example 5. The product was yellow sticky solid. Single spot on TLC, $R_f$=0.44 (CHCl$_3$/CH$_3$OH 30: 1); mp 153–155° C. Anal.: calcd. for $C_{28}H_{37}N_3O_7$:527.62; C, 63.74; H, 7.07; N, 7.96. Found: C, 63.66; H, 7.09; N, 7.92. NMR (CDCl$_3$) ok. MS (FAB) m/e=528.8 (M+1).

EXAMPLE 19

Z—Leu—Abu—CONH—CH$_2$—C$_4$H$_4$N

This compound was synthesized from the corresponding protected α-ketoester and 4-(aminomethyl)pyridine in 45% yield by the procedure described in Example 13. The product was greenish yellow solid. Single spot on TLC, $R_f$=0.55 (CHCl$_3$/CH$_3$OH 10:1); mp 124–126° C. Anal: calcd. for $C_{25}H_{32}N_4O_5$:468.55; C, 64.08; H, 6.88; N, 11.96. Found: C, 63.88; H, 6.87; N, 11.96. NMR (CDCl$_3$) ok. MS (FAB) m/e=469 (M+1).

Methods and Starting Materials

Unless otherwise noted, materials were obtained from commercial suppliers and used without further purification. The purity of each compound was checked by TLC, mp, $^1$H NMR and mass spectroscopy. TLC were performed on Baker Si250F silica gel plates. Melting points were obtained on a Büchi capillary apparatus and are not corrected. $^1$H NMR spectra were determined on a Varian Gemini 300. Chemical shifts are expressed in ppm relative to internal tetramethylsilane. Mass spectra were obtained on a Varian MAT 112S spectrometer. Column chromatography was performed on silica gel (32–63 microns).

The physical properties and proton NMR data for the peptide α-keto amide inhibitors are given in Tables III and IV repectively.

Triphenyl Cyanomethyl Phosphonium Bromide (1) [Novikov, S. S. and Shvekhgeimer, G. A. *Izvest. Akad. Nauk S.S.R.R., OtdeL Khim. Nauk*, 2061–2063 (1960) incorporated herein by reference]. A solution of bromoacetonitrile (6.07 g, 50 mmol) and triphenyl phosphine (16.07 g, 60 mmol) in 50 ml of benzene was refluxed under an argon atmosphere for 30 minutes. After cooling to room temperature, the product was collected by filtration and dried under reduced pressure to give 16.51 g (43 mmol, 86% yield) of a white powder: $^1$H NMR (DMSO-d$_6$) δ5.81 (d, 2H, P—CH$_2$—CN), 7.86 (m, 12H, aromatic), 8.00 (m, 3H, aromatic); FABMS (calculated for $C_{20}H_{17}NP$, 302.1099) m/e 302.1097 (M$^+$-HBr+1).

5-Cyano-5-triphenylphosphoranylidene-4-keto-3-(N-t-butyloxylcarbonylamino)pentanoic Acid Benzyl Ester (5). To a suspension of triphenyl cyanomethyl phosphonium bromide (1, 0.68 g, 1.8 mmol) in anhydrous THF (10 mL) cooled in an ice bath was added triethylamine (396 mg, 546 μL, 3.9 mmol) and the mixture stirred in an ice bath for 15 min. To a solution of N-t-butyloxycarbonyl-β-benzylaspartic acid (2, 575 mg, 1.8 mmol) in THF (15 mL) cooled to −15° C. was added N-methyl morpholine (180 mg, 196 μL, 1.8 mmol) followed by iso-butylchloroformate (243 mg, 231 μL, 1.8 mmol). The resulting solution was stirred at −15° C. for 5 min before being added dropwise with stirring to the previously prepared cyanomethylphosphorane solution. The mixture was stirred at 0° C. for 15 min and then allowed to warm to room temperature and then stirred for a further 16 h. The precipitate was removed by filtration and the solvent removed under reduced pressure. The mixture was purified by chromatography on silica gel (0–50% ethyl acetate in hexane) to yield the product as a clear oil which solidified on drying (0.76 g, 70%): mp 42–44° C.; $^1$H NMR (CDCl$_3$) δ1.39 (s, 9H, Boc CH$_3$'s), 2.99 (d, 2H, β-CH$_2$), 5.06 (m, 3H, α-CH & benzyl CH$_2$), 5.62 (d, 1H, NH), 7.28 (m, 5H, benzyl aromatic CH's), 7.52 (m, 15H, PPh$_3$ aromatic CH's); MS (El, calculated for $C_{36}H_{35}N_2O_5P$, 606.2284) m/e 606.2292 (M$^+$).

5-Cyano-5-triphenylphosphoranylidene-4-keto-3-(N-benzyloxylcarbonylamino)pentanoic Acid t-Butyl Ester (6). This was synthesized in a manner identical to that used for 5, except that N-benzyloxycarbonyl-β-t-butyl aspartic acid (3, 4.01 g, 12.4 mmol) was used instead of N-t-butyloxycarbonylaspartic acid β-benzyl ester (2, Boc-Asp (Bzl)—OH) to give the product as pale yellow flakes (4.70 g, 7.74 mmol, 62% yield) after purification by silica gel chromatography ($R_f$=0.43, EtOAc:hexane=2:1): $^1$H NMR (DMSO-d$_6$) δ1.35 (s, 9H, Boc CH$_3$'s), 2.39 (dd, 1H, β-CH$_2$), 2.69 (dd, 1H, β-CH$_2$), 5.04 (m, 3H, α-CH & benzyl CH$_2$), 7.33 (m, 5H, benzyl aromatic CH's), 7.65 (m, 15H, PPh$_3$ aromatic CH's), 7.80 (m, 1H, NH); FABMS (calculated for $C_{36}H_{36}N_2O_5P$, 607.2362) m/e 607.2355 (M$^+$+1).

5-Cyano-5-triphenylphosphoranylidene-4-keto-3-(N-methyloxylcarbonylamino)pentanoic Acid Benzyl Ester (7). This was synthesized in a manner identical to that used for 5, except that methyloxycarbonylaspartic acid β-benzyl ester (4, 506 mg, 1.8 mmol) instead of 2 to give the product as a clear oil which was recrystallized from ether/hexane (447 mg, 44%): $^1$H NMR (CDCl$_3$) δ3.00 (m, 2H, β-CH$_2$), 3.57 (s, 3H, CH$_3$O), 5.05 (s, 2H, benzyl CH$_2$), 5.11 (m, 1H, α-CH), 5.85 (d, 1H, NH), 7.23 (m, 5H, benzyl aromatic CH's), 7.48 (m, 15H, PPh$_3$ aromatic CH's); FABMS (calculated for $C_{33}H_{30}N_2O_5P$, 565.1892) m/e 565.1891 (M$^+$+1).

EXAMPLE 20

Boc—Asp(Bzl)—CONH—CH$_2$CH$_2$Ph (8)

Ozone gas was bubbled through a solution of 5 (606 mg, 1 mmol) in CH$_2$Cl$_2$ (20 mL) cooled to −78° C. until its blue color persists within the solution. The excess ozone was purged using argon and phenethylamine (181 mg, 189 μL, 1.5 mmol) was added. The resulting solution was stirred at −78° C. for 1 h and then allowed to warm to r.t. The solvent was removed under reduced pressure and the residue chromatographed on silica gel (0–30% ethyl acetate in hexane) to yield the product as a clear oil which was then recrystallized from ether/hexane (145 mg, 32%): mp 132–134° C.; $^1$H NMR (CDCl$_3$) δ1.43 (s, 9H, Boc CH3's), 2.81 (t, 2H, NHCH$_2$—CH$_2$—Ph), 3.12 (dd, 1H, 1 of CH$_2$—CO$_2$Bzl), 3.44 (dd, 1H, 1 of CH$_2$—CO$_2$Bzl), 3.55 (t, 2H, NH—CH$_2$—CH$_2$Ph), 5.10 (s, 2H, benzyl CH2), 5.13 (m, 1H, α-CH), 5.51 (d, 1H, urethane NH), 6.92 (br, 1H, amide NH), 7.20 (m, 5H, phenethyl aromatic CH's), 7.30 (m, 5H, benzyl aromatic CH's); FABMS (calculated for C$_{25}$H$_{31}$N$_2$O$_6$, 455.2182) m/e 455.2146 (M$^+$+1).

EXAMPLE 21
Boc—Asp(Bzl)—CONH—CH$_2$CH$_2$CH$_2$Ph (9)

This was prepared in a manner identical to that for 8, except using 3-phenyl-1-propylamine (203 mg, 213 μL, 1.5 mmol) instead of phenethylamine to yield the product as a white crystalline solid (117 mg, 25%): mp 87–88° C.; $^1$H NMR (CDCl$_3$): 1.45 (s, 9H, Boc CH3's), 1.81 (tt, 2H, NHCH$_2$—CH$_2$—CH$_2$Ph), 2.63 (t, 2H, NHCH2CH$_2$—CH$_2$—Ph), 2.70 (dd, 1H, 1 of CH$_2$—CO$_2$Bzl), 3.05 (dd, 1H, 1 of CH$_2$—CO$_2$Bzl), 3.27 (t, 2H, NH—CH$_2$—CH$_2$CH$_2$Ph), 4.48 (m, 1H, α-CH), 5.11 (s, 2H, benzyl CH$_2$), 5.65 (br, 1H, urethane NH), 6.49 (br, 1H, amide NH), 7.28 (m, 10H, aromatic CH's); FABMS (calculated for C$_{26}$H$_{33}$N$_2$O$_6$, 469.2339) m/e 469.2359 (M$^+$+1).

EXAMPLE 22
Cbz—Asp(t-Bu)—CONH-CH$_2$CH$_2$Ph (10)

This was prepared in a manner identical to that used for 8, except using 6 (2.53 g, 4.17 mmol) instead of 5 to give the product as a white crystalline solid (433.8 mg, 0.95 mmol, 22% yield) after purification by silica gel chromatography (R$_f$=0.21, EtOAc: hexane=1:3) and recrystallization from ethyl acetate and hexane: mp 89–90° C.; $^1$H NMR (CDCl$_3$) δ1.37 (s, 9H, t-Bu CH$_3$'s), 2.83 (t, 2H, NHCH$_2$—CH$_2$—Ph), 2.99 (dd, 1H, 1 of β-CH$_2$), 3.39 (dd, 1H, 1 of β-CH$_2$), 3.56 (q, 2H, NH—CH$_2$—CH$_2$Ph), 5.08 (m, 1H, α-CH), 5.12 (s, 2H, benzyl CH$_2$), 5.75 (d, 1H, urethane NH), 6.98 (t, 1H, amide NH), 7.29 (m, 10H, aromatic CH's); FABMS (calculated for C$_{25}$H$_{31}$N$_2$O$_6$, 455.2182) m/e 455.2201 (M$^+$+1).

EXAMPLE 23
General Procedure for the Debenzylation of Aspartyl β-Benzyl Ester Derivatives to Yield 12–14, 24–36 (Boc—Asp—CONH—CH$_2$CH$_2$Ph, 12)

To a solution of the benzyl ester Boc—Asp(OBzl)—CONH—CH$_2$CH$_2$Ph (8, 75 mg, 0.16 mmol) in methanol (5 mL) was added Pd(OH)$_2$/C (7.5 mg, 10% w/w) and the solution was stirred under a hydrogen atmosphere until no further H$_2$ take-up was observed (~1 h). The solution was filtered through Celite and the solvent removed under reduced pressure to yield the product 12 as a clear oil which was recrystallized from methanol/ether (50 mg, 83%).

EXAMPLE 24
Cbz—Asp—CONH—CH$_2$CH$_2$Ph (15)

The t-butyl ester (10, 100 mg, 0.22 mmol) in trifluoroacetic acid (5 mL) was stirred in an ice bath for 30 minutes. Trifluoroacetic acid was removed under reduced pressure, the crude product was recrystallized from EtOAc/hexane to give 76.8 mg (0.19 mmol, 87% yield) of a pale yellow solid.

EXAMPLE 25
3-(4-Chlorophenyl)propanoic Acid (4-Chlorohydrocinnamic Acid)

To a solution of 1.80 g (10 mmol) of 4-chlorocinnamic acid in 50 mL of THF was added Pd/C (1.04 g, 5% w/w) and the solution was stirred under a hydrogen atmosphere until no further H$_2$ take-up was observed (~1 h). The solution was filtered through Celite and the solvent removed under reduced pressure to yield 1.82 g (9.8 mmol, 98%) of a white solid: mp. 103–105° C.; $^1$H NMR (DMSO-d$_6$) δ2.51 (t, 2H, β-CH$_2$), 2.79 (t, 2H, α-CH$_2$), 7.28 (dd, 4H, aromatic CH's), 12.12 (s, 1H, COOH); MS (EI, calculated for C$_9$H$_9$ClO$_2$, 184.0291) m/e 184.0288 (M$^+$).

EXAMPLE 26
HCl.H—Asp—CONH—CH$_2$CH$_2$Ph (24)

The keto amide (8) (227 mg, 0.5 mmol) was dissolved in ethyl acetate (10 mL) and cooled in an ice bath. Dry HCl gas was bubbled through until the solution was saturated and then the solution was stirred at r.t. until the starting material had been consumed as indicated by tlc (~30 min). The solvent was removed under reduced pressure to give HCl.H—Asp(Bzl)—CONH—CH$_2$CH$_2$Ph (22) as a white solid: FABMS (calculated for C$_{20}$H$_{23}$N$_2$O$_4$, 355.1658) m/e 355.1651 (M$^+$+1−HCl). Without further purification, this crude product was used for the debenzylation reaction in a same manner as described for 12 to give 12 mg (0.04 mmol, 8%) of a white solid after recrystallization from methanol/ether.

EXAMPLE 27
HCl.H—Asp—CONH—CH$_2$CH$_2$CH$_2$Ph (25)

This was prepared in a manner identical to 24 except using 234 mg (0.5 mmol) of 9 to give 15 mg (0.05 mmol, 10%) of the product.

EXAMPLE 28
PhCH$_2$SO$_2$—Asp—CONH—CH2CH$_2$Ph (26)

The keto amide (8) (109 mg, 0.24 mmol) was dissolved in ethyl acetate (5 mL) and cooled in an ice bath. Dry HCl gas was bubbled through until the solution was saturated and then the solution was stirred at r.t. until the starting material had been consumed as indicated by tlc (~30 min). The solvent was removed under reduced pressure. The residue (22) was dissolved in dry CH$_2$Cl$_2$ (5 mL) and triethylamine (61 mg, 84 μL) added. The solution was then added dropwise to a solution of benzyl sulfonyl chloride (46 mg, 0.24 mmol) in dry CH$_2$Cl$_2$ (5 mL) cooled in an ice bath. The resulting solution was allowed to stir at r.t. for 16 h. It was washed with 1M HCl, 5% sodium bicarbonate solution and saturated brine, then dried (MgSO$_4$) and the solvent removed under reduced pressure to yield the product as a white solid (51 mg, 42%): mp 128–130° C. $^1$H NMR (CDCl$_3$) δ2.61 & 2.99 (ABX, 2H, β-CH$_2$), 2.86 (t, 2H, CH$_2$Ph), 3.57 (m, 2H, NH—CH$_2$), 4.74 (m, 1H, α-CH), 5.14 (2xs, 4H, benzyl CH$_2$'s), 6.53 & 6.74 (m, 2H, NH's), 7.29 (m, 15H, aromatic CH's); FABMS m/e 509 (M$^+$+1).

This product was subjected to the debenzylation conditions as described for 12 to give 10 mg (24%) of white solid.

EXAMPLE 29
General Procedure for the Synthesis of 27–35 (Ac—Tyr—Val—Ala—Asp—CONH—CH$_2$CH$_2$Ph, 35)

The ketoamide (8) (227 mg, 0.5 mmol) was dissolved in ethyl acetate (10 mL) and cooled in an ice bath. Dry HCl gas was bubbled through until the solution was saturated and then the solution was stirred at r.t. until the starting material had been consumed as indicated by tlc (~30 min). The solvent was removed under reduced pressure to give 22. To a solution of Ac—Tyr—Val—Ala—OH (197 mg, 0.5 mmol) in dry THF (10 mL) and DMF (2 mL) cooled to −15° C. was added N-methyl morpholine (51 mg, 55 µL, 0.5 mmol) followed by iso-butyl chlorofornate (68 mg, 65 µL, 0.5 mmol) and the solution stirred at −15° C. for 5 min. A previously prepared solution of 22 and N-methyl morpholine (51 mg, 55 µL, 0.5 mmol) in dry THF (5 mL) was added, the solution stirred at −15° C. for 15–30 min and then at r.t. for 16 h. The solution was filtered and the solvent removed under reduced pressure to yield the product which was recrystallized from methanol/ether to give 340 mg (93%) of Ac—Tyr—Val—Ala—Asp(Bzl)—CONH—$CH_2CH_2$Ph: mp 192–194° C.; $^1$H NMR (DMSO) δ0.77 (m, 6H, Val $CH_3$'s), 1.19 (m, 3H, Ala $CH_3$), 1.74 (s, 3H, Ac $CH_3$), 1.93 (m, 1H, Val β-CH), 2.62 (obs, 2H, $CH_2$Ph), 2.77 & 3.18 (m, 4H, Tyr & Asp β-$CH_2$'s), 3.37 (m, 2H, NH-$CH_2$), 3.75, 4.09, 4.19 & 4.53 (m, 4H, α-CH's), 5.06 (s, 2H, benzyl $CH_2$), 6.62 & 7.01 (2xd, 4H, Tyr aromatic CH's), 7.20 (m, 5H, phenethyl aromatic CH's), 7.35 (s, 5H, benzyl aromatic CH's), 7.83 (m, 1H, NH), 8.04 (m, 4H, NH's), 9.15 (s, 1H, Tyr OH); FABMS m/e 730 ($M^+$+1).

This product was subjected to the debenzylation conditions as described for 12 to give 170 mg (57%) of a white solid.

EXAMPLE 30

Ac—Tyr—Val—Ala—Asp—CONH—$CH_2CH_2CH_2$Ph (36)

This was prepared in a manner identical to 35 except using (9) (234 mg, 0.5 mmol) instead of (8) to yield the product which was recrystallized from methanol/ether to give the product as a white solid.

EXAMPLE 31

N,N-Dibenzylaspartic Acid Dibenzyl Ester (37) [Gmeiner, P., Junge, D. and Kartner, A. *J. Org. Chem.* 59, 6766–6776 (1994) incorporated herein by reference]. To a solution of 26.62 g (0.20 mole) of aspartic acid in 300 mL of 3 M $Na_2CO_3$ was added 202 g (1.6 mole) of benzyl chloride at room temperature. The mixture was refluxed for 10 hours. After cooling to room temperature, the mixture was extracted with ethyl acetate (2×150 mL). The combined extracts were dried over $MgSO_4$ and then filtered. Solvent was removed from the filtrate with a rotary evaporator and benzyl alcohol was removed at 60° C./0.5 mm Hg to yield 93.02 g (0.18 mole, 94%) of a light brown oil: $R_f$=0.74 (EtOAc:hexane=1:4); $^1$H NMR ($CDCl_3$) δ2.82 (ddd, 2H, β-$CH_2$), 3.65 (dd, 4H, Ph—$CH_2$—N), 3.97 (t, 1H, α-CH), 5.08 (m, 4H, COO—$CH_2$—Ph), 7.28 (m, 20H, aromatic H). FABMS (calculated for $C_{32}H_{31}NO_4$, 493) m/e 494 ($M^+$+1). The crude product was used for the next reaction without further purification.

2-(N,N-Dibenzylamino)butane-1,4-diol (38) [Gmeiner, P., Junge, D. and Kartner, A. *J. Org. Chem* 59, 6766–6776 (1994) incorporated herein by reference]. To a stirred solution of 19.40 g (0.039 mole) of 37 in 60 mL of anhydrous THF was added a solution of $LiAlH_4$ in THF in 4 portions (0.46 g, 0.012 mole in 20 mL for each portion) at 5° C. The resulting mixture was stirred at room temperature for 1 hour under an argon atmosphere and then allowed to stand at room temperature overnight to permit the lithium salt to precipitate. The organic layer was poured into a beaker containing 300 mL $Et_2O$. A saturated aqueous $Na_2SO_4$ solution was added with stirring to the ether solution dropwise until gas evolution ceased. The resulting mixture was stirred for 5 minutes and then filtered. The solvent was removed from the filtrate with a rotary evaporator. The crude residue was purified by gel chromatography (EtOAc:hexane=2:1) to give 10.12 g (0.035 mole, 89%) of a colorless oil: $R_f$=0.27 (EtOAc:hexane=1:4); $^1$H NMR ($CDCl_3$) δ1.45 (m, 1H, β-CH), 1.96 (m, 1H, β-CH), 2.90 (m,, 1H, α-CH), 3.28 (br, 2H, —OH), 3.59 (m, 8H, Ph—C$H_2$—N, $CH_2$—OH), 7.28 (m, 10H, aromatic H). MS (CI, calculated for $C_{18}H_{24}NO_2$, 286.1807) m/e 286.1843 ($M^+$+1).

2-(N,N-Dibenzylamino)-4-[(t-butyldimethylsilyl)oxy] butanol (39) [Gmeiner, P., Junge, D. and Kartner, A. *J. Org. Chem.* 59, 6766–6776 (1994) incorporated herein by reference]. To a solution of 3.61 g (0.012 mole) of 38 in 40 mL of DMF was added sequentially at 5° C. solutions of 2.36 g (0.016 mole) of t-butyldimethylsilyl chloride in 20 mL of DMF and 1.77 g (0.026 mole) of imidazole in 20 mL of DMF. After stirring the resulting mixture at the same temperature for 3 hours under anhydrous conditions, 50 mL of saturated aqueous $NH_4Cl$ solution was added and the mixture was extracted with $Et_2O$ (4×50 mL). The combined extracts were dried over $MgSO_4$ and filtered. The solvent was removed in vacuo and the crude residue was purified by gel chromatography (EtOAc:hexane=1:5) to give 2.71 g (0.0068 mole, 56%) of a colorless oil: $R_f$=0.31 (EtOAc:hexane=1:4); $^1$H NMR (DMSO-$d_6$) δ−0.22 (s, 6H, Si-$CH_3$), 0.62 [s, 9H, Si-C($CH_3$)$_3$], 1.38 (m, 1H, β-CH), 1.53 (m, 1H, β-CH), 3.17 (s, 1H, α-CH), 3.30 (m, 2H, —C$H_2$—OSi—), 3.46 (m, 6H, Ph—$CH_2$—N, $CH_2$—OH), 4.22 (t, 1H, —OH), 6.98–7.16 (m, 10H, aromatic H); FABMS (calculated for $C_{24}H_{38}NO_2Si$, 400.2672) m/e 400.2639 ($M^+$+1).

2-(N,N-Dibenzylamino)-4-[(t-butyldimethylsilyl)oxy] butanal (40) [Gmeiner, P., Junge, D. and Kartner, A. *J. Org. Chem.* 59, 6766–6776 (1994) incorporated herein by reference]. To a solution of 2.18 g (28 mmol) of DMSO in 5 mL of $CH_2Cl_2$, solutions of 1.78 g (14 mmol) of oxalyl chloride in 5 mL of $CH_2Cl_2$ and 4.80 g (12 mmol) of 39 in 20 mL of $CH_2Cl_2$ were added sequentially at −78° C. After stirring at the same temperature under an argon atmosphere for 30 minutes, 6.07 g (60 mmol) of $NEt_3$ in 60 mL of $Et_2O$ was added in one portion. The mixture was stirred for 10 minutes, washed with saturated aqueous $NaHCO_3$ solution (2×40 mL) and 1 M $NaHSO_4$ solution. The organic layer was dried over $MgSO_4$ and filtered. The solvent was removed from the filtrate with a rotary evaporator and the residue was dried under reduced pressure to give 4.44 g (11 mmol, 93%) of a colorless oil: $R_f$=0.57 (EtOAc:hexane=1:4); $^1$H NMR (DMSO-$d_6$) δ−0.06 (s, 6H, Si-$CH_3$), 0.76 [s, 9H, Si-C($CH_3$)$_3$], 1.86 (m, 2H, β-C$H_2$), 2.81 (m, 2H, —C$H_2$—OSi—), 3.61 (m, 5H, α-CH, Ph—$CH_2$—N), 7.28 (m, 10H, aromatic H), 9.70 (s, 1H, aldehyde H); FABMS (calculated for $C_{24}H_{36}NO_2Si$, 398.2515) m/e 398.2515 ($M^+$+1).

3-(N,N-Dibenzylamino)-5-[(t-butyldimethylsilyl)oxy]-2-[(trimethylsilyl)oxy]pentanenitrile (41). A mixture of 3.94 g (10 mmol) of 40 and 1.37 g (14 mmol) of trimethylsilyl cyanide was stirred at room temperature overnight and then dried in vacuo for 24 hours to give a quantitative yield of 41 as a light brown oil (racemic mixture): $R_f$=0.64 (EtOAc:hexane=1:4); $^1$H NMR ($CDCl_3$) δ0.078 (m, 15H, Si-C$H_3$), 0.85 [s, 9H, Si-C($CH_3$)$_3$], 1.87 (m, 2H, β-$CH_2$), 3.11 (m, 1H, α-CH), 3.78 (m, 6H, —$CH_2$—OSi—, Ph—C$H_2$—N), 4.44 [dd, 1H, —CH(CN)—OSi—], 7.20–7.41 (m, 10H, aromatic H); FABMS (calculated for $C_{28}H_{45}N_2O_2Si_2$, 497.3020) m/e 497.2999 ($M^+$+1).

N-(2-Phenylethyl)-3-(N,N-dibenzylamino)-2,5-dihydroxypentamide (42). A solution of 5.52 g (11 mmol) of 41 in 10 mL of concentrated HCl was stirred at room temperature for 1 hour. Excess HCl was removed under reduced pressure and the residue was dried in vacuo overnight to give a brown solid of 3-(N,N-dibenzylamino)-2,5-dihydroxypentanoic acid: FABMS (calculated for $C_{19}H_{23}NO_4$, 329) m/e 330 ($M^++1$). This crude product was dissolved in 15 mL of DMF. Upon stirring the solution in an ice bath, 1.30 g (13 mmol) of triethylamine was added and the mixture was stirred for 10 minutes. To this mixture was sequentially added 1.62 g (12 mmol) of HOBt in 5 mL of DMF, 2.00 g (16 mmol) of phenethylamine, 2.72 g (13 mmol) of DCC in 5 mL of DMF. The resulting solution was stirred at 10° C. for 72 hours. The mixture was heated until the solids dissolved (approximately at 85° C.) and allowed to stand at 10° C. overnight. The mixture was then filtered to remove DCU. Solvent was removed from the filtrate under reduced pressure. Ethyl acetate (200 mL) was added to the residue and the solution was sequentially washed with 10% $Na_2CO_3$ (2×100 mL), distilled water (100 mL), and saturated NaCl (100 mL). After drying over $MgSO_4$, the solution was filtered and ethyl acetate was removed from the filtrate with a rotary evaporator. The crude residue was purified by gel chromatography (EtOAc:hexane=4:1) to give two enantiomers; first enantiomer (2.63 g, 6.8 mmol, 55% yield, a yellow hygroscopic solid): $R_f$=0.43 (EtOAc:hexane=4:1); $^1$H NMR (DMSO-$d_6$) δ1.33 (m, 1H, β-CH), 1.86 (m, 1H, β-CH), 2.69 (t, 2H, C—C$\underline{H}_2$—Ph), 2.97 (m, 1H,α-CH), 3.23 (m, 4H, C$\underline{H}_2$—OH, CON$\underline{H}$—C$\underline{H}_2$—), 3.50 (d, 2H, Ph-C$\underline{H}_2$—N), 3.81 (d, 2H, Ph—C$\underline{H}_2$—N), 4.26 (t, 1H, CH$_2$—O$\underline{H}$), 4.36 (d, 1H, C$\underline{H}$—OH), 5.66 (d, 1H, CH—O$\underline{H}$), 7.23 (m, 15H, aromatic H), 7.85 (t, 1H, CON$\underline{H}$); FABMS (calculated for $C_{27}H_{33}N_2O_3$, 433) m/e 433 ($M^++1$). Second enantiomer (0.87 g, 2.0 mmol, 18% yield, a yellow oil): Rf =0.21 (EtOAc:hexane=4:1); $^1$H NMR (DMSO-$d_6$) δ1.72 (m, 2H, β-CH), 2.73 (t, 2H, C—C$\underline{H}_2$—Ph), 2.99 (q, 1H, α-CH), 3.32 (m, 4H, C$\underline{H}_2$—OH, CON$\underline{H}$—C$\underline{H}_2$—), 3.52 (d, 2H, Ph—C$\underline{H}_2$—N), 3.82 (d, 2H, Ph—C$\underline{H}_2$—N), 3.95 (t, 1H, CH$_2$—O$\underline{H}$), 4,35 (d, 1H, C$\underline{H}$—OH), 5,49 (d, 1H, CH—O$\underline{H}$), 7.22 (m, 15H, aromatic H), 7.82 (t, 1H, CON$\underline{H}$); FABMS (calculated for $C_{27}H_{33}N_2O_3$, 433) m/e 433($M^++1$).

N-(3-Phenylpropyl)-3-(N,N-dibenzylamino)-2,5-dihydroxypentamide (43). This was prepared in a manner identical to that for 42, except using 3-phenyl-1-propylamine, 3.97 g (0.019 mole) instead of phenethylamine to give two enantiomers; first enantiomer (3.40 g, 7.6 mmol, 47% yield, a yellow hygroscopic solid): $R_f$=0.30 (EtOAc:hexane=4:1); $^1$H NMR (DMSO-$d_6$) δ1.39 (m, 1H, β-CH), 1.68 (p, 2H, CONH—CH$_2$—C$\underline{H}_2$—CH$_2$—Ph), 1.88 (m, 1H, β-CH), 2.52 (t, 2H, C—C$\underline{H}_2$—Ph), 2.97 (d, 1H, α-CH), 3.07 (q, 2H, C$\underline{H}_2$—OH), 3.19 (m, 1H, CONH—C$\underline{H}_2$—), 3.55 (m, 3H, Ph—C$\underline{H}_2$—N, CONH—C$\underline{H}_2$—), 3.81 (d, 2H, Ph—C$\underline{H}_2$—N), 4.26 (t, 1H, CH$_2$-O$\underline{H}$), 4.36 (d, 1H, C$\underline{H}$—OH), 5.61 (d, 1H, CH—O$\underline{H}$), 7.24 (m, 15H, aromatic H), 7.85 (t, 1H, CON$\underline{H}$); FABMS (calculated for $C_{28}H_{35}N_2O_3$, 447.2648) m/e 447.2680 ($M^++1$). Second enantiomer (1.35 g, 3.0 mmol, 19% yield, a yellow oil): $R_f$=0.10 (EtOAc:hexane=4:1) $^1$H NMR (DMSO-$d_6$) δ1.73 (m, 4H, β-CH$_2$, CONH—CH$_2$—C$\underline{H}_2$—CH$_2$—Ph), 2.57 (m, 2H, C—C$\underline{H}_2$—Ph), 3.10 (m, 4H, α-C$\underline{H}$, C$\underline{H}_2$—OH, CONH—C$\underline{H}_2$—), 3.38 (m, 1H, CONH—C$\underline{H}_2$—), 3.53 (d, 2H, Ph—C$\underline{H}_2$—N), 3.86 (d, 2H, Ph—C$\underline{H}_2$—N), 3.97 (t, 1H, C$\underline{H}$—OH), 4,35 (t, 1H, CH$_2$—OH), 5,43 (d, 1H, CH—O$\underline{H}$), 7.22 (m, 15H, aromatic H), 7.80 (t, 1H, CON$\underline{H}$); FABMS (calculated for $C_{28}H_{35}N_2O_3$, 447.2648) m/e 447.2640 ($M^++1$).

N-(2-Phenylethyl)-3-amino-2,5-dihydroxypentamide (44). To a solution of 4.71 g (11 mmol) of 42 (enantiomeric mixture) in 30 mL of methanol, 1.25 g of 20% Pd(OH)$_2$ in 50 mL of methanol was added. The mixture was hydrogenated at room temperature for 22 hours and then filtered through two layers of filter paper. Methanol was removed from the filtrate with a rotary evaporator. The residue was dried in vacuo overnight to give 2.74 g (11 mmol, 100%) of a white solid (enantiomeric ratio=3:1): $^1$H NMR (DMSO-$d_6$) δ1.36 (m, 2H, β-C$\underline{H}_2$), 2.71 (m, 2H, C—C$\underline{H}_2$—Ph), 2.95 (dt, 1H, α-CH), 3.34 (m, 8H, CH$_2$—OH, CONH—CH$_2$—, CH—OH, CH$_2$—O$\underline{H}$, —N$\underline{H}_2$), 3.67 (d, 0.33H, C$\underline{H}$—O$\underline{H}$), 3.74 (d, 0.66H, CH—O$\underline{H}$), 7.25 (m, 5H, aromatic H), 7.78 (t, 1H, CON$\underline{H}$); FABMS (calculated for $C_{13}H_{21}N_2O_3$, 253.1552) m/e 253.1548 ($M^++1$).

N-(3-Phenylpropyl)-3-amino-2,5-dihydroxypentamide (45). This was prepared in a manner identical to that for 44, except using 4.70 g (10 mmol) of 43 (enantiomeric mixture) to give 2.80 g (10 mmol, 100%) of a white solid (enantiomeric ratio=2:1): $^1$H NMR (DMSO-$d_6$) δ1.43 (m, 2H, 4-C$\underline{H}_2$), 1.69 (m, 2H, CONH—CH$_2$—C$\underline{H}_2$—CH$_2$—Ph), 2.52 (m, 3H, C—C$\underline{H}_2$—Ph, α-CH), 3.06 (m, 5H, C$\underline{H}_2$—OH, CONH—C$\underline{H}_2$—, C$\underline{H}$— OH), 3.49 (m, 1H, CH$_2$—O$\underline{H}$), 3.53 (br, 2H, -N$\underline{H}_2$), 3.69 (d, 0.33H, d, CH-O$\underline{H}$), 3.78 (d, 0.66H, CH-O$\underline{H}$), 7.21 (m, 5H, aromatic H), 7.84 (t, 1H, t, CON$\underline{H}$). FABMS (calculated for $C_{14}H_{23}N_2O_3$, 267.1709) m/e 267.1699 ($M^++1$).

N-(2-Phenylethyl)-3-(N-benzyloxycarbonylalanylamino)-2,5-dihydroxypentamide (46). Upon stirring a solution of 2.71 g (10.74 mmol) of 44 (mixture of enantiomers) in 10 mL of DMF in an ice bath, 1.08 g (8 mmol) of HOBt and 2.00 g (8.95 mmol) of N-benzyloxycarbonylalanine in 10 niL of DMF, and 2.21 g (10.74 mmol) of DCC in 10 mL of DMF were added sequentially. The mixture was stirred at 10° C. for 24 hours. The mixture was heated until the solids dissolved (90° C.). The solution was stood at 10° C. overnight and filtered to remove DCU. Solvent was removed from the filtrate under reduced pressure. Ethyl acetate (100 mL) was added to the residue and the solution was washed with saturated NaHCO$_3$ (50 mL), 1M HCl (50 mL) and distilled water (50 mL). Methanol (20 mL) and MgSO$_4$ were added to the final solution, which was allowed to stand at room temperature overnight, and filtered. Solvent was removed from the filtrate with a rotary evaporator and the residue was recrystallized from EtOAc:methanol:hexane=2:0.5:1 to give 2.82 g (6.16 mmol, 68%) of a white solid ($R_f$=0.34,0.27, EtOAc:MeOH=10:1, enantiomer ratio=3.8:1.0): mp 142–144° C.; $^1$H NMR (DMSO-$d_6$) δ1.18 (d, 3H, Ala β-CH$_3$), 1.44 (m, 2H, pentamide 4—C$\underline{H}_2$), 2.72 (t, 2H, C—CH$_2$—Ph), 3.31 (m, 4H, CH$_2$—OH, CONH—CH$_2$—), 3.87 (dd, 1H, pentamide 3-C$\underline{H}$), 4.08 (m, 2H, Ala α-C$\underline{H}$, pentamide 2-C$\underline{H}$), 4.27 (t, 1H, CH$_2$—O$\underline{H}$), 5.01 (dd, 2H, Ph—CH$_2$—OCO), 5.77 (d, 0.79H, CH—O$\underline{H}$), 5.86 (d, 0.21H, CH—O$\underline{H}$), 7.26 (m, 10H, aromatic H), 7.41 (d, 1H, CONH), 7.57 (d, 1H, CON$\underline{H}$), 7.84 (t, 1H, CON$\underline{H}$); FABMS (calculated for $C_{24}H_{32}N_3O_6$, 458.2291) m/e 458.2325 ($M^++1$).

N-(3-Phenylpropyl)-3-(N-benzyloxycarbonylalanylamino)-2,5-dihydroxypentamide (47). This was prepared in a manner identical to that for 46, except using 2.00 g (7.5 mmol) of 45 (enantiomeric mixture) to give 1.62 g (3.4 mmol, 45%) of a white solid (enantiomer ratio=3:1):$R_f$=0.09 (EtOAc); mp 109–119° C.; $^1$H NMR (DMSO-$d_6$) δ1.18 (d, 3H, Ala β-CH$_3$), 1.50 (m, 2H, pentamide 4-C$\underline{H}_2$), 1.70 (p, 2H, CH$_2$—C$\underline{H}_2$—CH$_2$Ph), 2.54 (t, 2H, CH$_2$—CH$_2$—CH$_2$Ph), 3.09 (m, 2H, N—C$\underline{H}_2$—CH$_2$—CH$_2$Ph), 3.31 (m, 2H, pentamide 5-C$\underline{H}_2$), 3.88 (m, 1H, Ala α-C$\underline{H}$), 4.08 (m, 2H, pentamide 2-CH, 3-CH), 4.30 (t, 1H, pentamide 5-CH$_2$—OH), 5.01 (dd, 2H, Ph—CH$_2$—OCO), 5.73, 5.81 (d, 0.75H, pentamide 2-CH—OH), 5.81 (d, 0.25H, pentamide 2-CH—OH), 7.31 (m, 11H, aromatic CH's, CONH—Ala), 7.57 (d, 1H, PhCH$_2$OCONH), 7.85 (t, 1H, CONHCH$_2$—CH$_2$—CH$_2$Ph); FABMS (calculated for C$_{25}$H$_{34}$N$_3$O$_6$, 472.2448) m/e 472.2411 (M$^+$+1).

N-(2-Phenylethyl)-3-(N-benzyloxycarbonylvalylalanylamino)-2,5-dihydroxypentamide (48). This was prepared in a manner identical to that for 46, except using 1.28 g (4.0 mmol) of Cbz—Val—Ala—OH to give 0.92 g (1.1 mmol, 44%) of a white solid (enantiomeric ratio could not be determined due to the overlap of the pentamide 2-CH—OH peaks in the $^1$H MNR spectrum): mp 218–220° C.; $^1$H NMR (DMSO-d$_6$) δ0.82 (dd, 6H, Val β-CH$_3$'s), 1.17 (d, 3H, Ala β-CH$_3$), 1.43 (m, 2H, pentamide 4-CH$_2$), 1.95 (m, 1H, Val β-CH), 2.71 (t, 2H, CONH—CH$_2$—CH$_2$Ph), 3.29 (m, 4H, pentamide 5-CH$_2$, N—CH$_2$—CH$_2$Ph), 3.85 (m, 2H, Ala, Val α-CH), 4.08 (m, 1H, pentamide 3-CH), 4.26 (m, 2H, pentamide 2-CH, 5-CH$_2$—OH), 5.01 (s, 2H, PhCH$_2$OCONH), 5.76 (d, 1H, pentamide 2-CH—OH), 7.29 (m, 11H, aromatic CH's, Ala—NH), 7.61 (d, 1H, PhCH$_2$OCONH), 7.82 (t, 1H, CONH—CH$_2$—CH$_2$Ph), 7.95 (d, 1H, Val—NH); FABMS (calculated for C$_{29}$H$_{41}$N$_4$O$_7$, 557.2975) m/e 557.2935 (M$^+$+1).

N-(3-Phenylpropyl)-3-(N-benzyloxycarbonylvalylalanylamino)-2,5-dihydroxypentamide (49). This was prepared in a manner identical to that for 46, except using 2.98 g (9,2 mmol) of Cbz—Val—Ala—OH and 2.71 g (10.17 mmol) of 45 to give 2.37 g (4.15 mmol, 44%) of a white solid (enantiomeric ratio could not be determined): R$_f$=0.07 (EtOAc); mp 192–193° C.; $^1$H NMR (DMSO-d$_6$) δ0.82 (dd, 6H, Val β-CH$_3$'s), 1.17 (d, 3H, Ala β-CH$_3$), 1.50 (m, 2H, pentamide 4-CH$_2$), 1.70 (m, 2H, CONH—CH$_2$—CH$_2$—CH$_2$Ph), 1.94 (m, 1H, Val β-CH), 2.53 (t, 2H, CONH—CH$_2$—CH$_2$—CH$_2$Ph), 3.07 (m, 2H, CONH-CH$_2$—CH$_2$—CH$_2$Ph), 3.32 (m, 2H, pentamide 5-CH$_2$), 3.86 (m, 2H, Ala, Val α-CH), 4.10 (m, 1H, pentamide 3-CH), 4.28 (m, 2H, pentamide 2-CH, 5-CH$_2$—OH), 5.00, (s, 2H, PhCH$_2$OCONH), 5.73 (d, 1H, pentamide 2-CH—OH), 7.24 (m, 11H, aromatic CH's, Ala—NH), 7.62 (d, 1H, PhCH$_2$OCONH), 7.83 (t, 1H, CONH—CH$_2$—CH$_2$Ph), 7.97 (d, 1H, Val—NH); FABMS (calculated for C$_{30}$H$_{43}$N$_4$O$_7$, 571.3132) m/e 5571.3169 (M$^+$+1).

N-(2-Phenylethyl)-3-(N-benzyloxycarbonylalanylamino)-5-t-butyldimethylsilyloxy-2-hydroxypentamide (50). Upon stirring a solution of 46 (1.13 g, 2.5 mmol) in 7 mL of DMF, t-butyldimethylsilyl chloride (0.745 g, 3.0 mmol) and imidazole (0.37 g, 5.5 mmol) were added sequentially. The resulting mixture was stirred at room temperature for 47 hours. Saturated NH$_4$Cl solution (20 mL) was added and the mixture stirred at room temperature for 5 minutes and was extracted with EtOAc (4×25 mL). The combined extracts were dried over MgSO$_4$ and filtered. Solvent was removed from the filtrate with a rotary evaporator and the crude product was purified by gel chromatography (EtOAc) to give 0.80 g (1.40 mmole, 56%) of a white solid (enatiomeric ratio=3.2:1): R$_f$=0.51, 0.41 (EtOAc); $^1$H NMR (DMSO-d$_6$) δ0.02 (s, 6H, Si-CH$_3$'s), 0.84 (s, 9H, Si-t-Bu), 1.20 (d, 3H, Ala β-CH$_3$), 1.52 (m, 2H, pentamide 4-CH$_2$), 2.72 (t, 2H, C—CH$_2$—Ph), 3.38 (m, 4H, CH$_2$—OH, CONH—CH$_2$—), 3.85 (dd, 1H, pentamide 3-CH), 4.07 (m, 2H, Ala α-CH, pentamide 2-CH, 5.00 (s, 2H, Ph—CH$_2$—OCO), 5.75 (d, 0.76H, pentamide 2-CH—OH), 5.86 (d, 0.24H, pentamide 2-CH—OH), 7.31 (m, 11H, aromatic H, CONH, 7.45 (d, 1H, CONH), 7.74 (t, 1H, t, CONH); FABMS (calculated for C$_{30}$H$_{46}$N$_3$O$_6$Si, 572.3156) m/e 572.3151 (M$^+$+1).

N-(3-Phenylpropyl)-3-(N-benzyloxycarbonylalanylamino)-5-t-butyldimethylsilyloxy-2-hydroxypentamide (51). This was prepared in a manner identical to that for 50, except using 1.59 g (3.4 mmol) of 47 to give 1.56 g (2.6 mmol, 78%) of a colorless oil (enantiomeric ratio=2.2:1): R$_f$=0.43, 0.38 (EtOAc); $^1$H NMR (DMSO-d$_6$) δ–0.03 (s, 6H, Si-CH$_3$'s), 0.78 (s, 9H, Si-t-Bu), 1.17 (d, 3H, Ala β-CH$_3$), 1.50 (m, 2H, pentamide 4-CH$_2$), 1.69 (m, 2H, CONHCH$_2$—CH$_2$—CH$_2$Ph), 2.53 (t, 2H, CONHCH$_2$—CH$_2$—CH$_2$—Ph), 3.10 (m, 4H, CH$_2$—OH, CONH—CH$_2$—), 3.85 (dd, 1H, pentamide 3-CH), 4,07 (m, 2H, Ala α-CH, pentamide 2-CH), 5.00 (s, 2H, Ph—CH$_2$—OCO), 5.73 (d, 0.8H, pentamide 2-CH-OH), 5.82 (d, 0.2H, pentamide 2-CH—OH), 7.18 (m, 11H, aromatic 1, CONH), 7.55 (d, 1H, CONH), 7.86 (t, 1H, t, CONH); FABMS (calculated for C$_{31}$H$_{48}$N$_3$O$_6$Si, 586.3312) m/e 586.3354 (M$^+$+1).

N-(2-Phenylethyl)-3-(N-benzyloxycarbonylvalylalanylamino)-5-t-butyldimethylsilyloxy-2-hydroxypentamide (52). This was prepared in a manner identical to that for 50, except using 0.63 g (1.1 mmol) of 48 to give 0.54 g (0.8 mmol, 71%) of a solid (enatiomeric ratio was not determined): R$_f$=0.27 (EtOAc); $^1$H NMR (DMSO-d$_6$) δ–0.04 (s, 6H, Si—CH$_3$'s), 0.83 (m, 15H, Si—t—Bu, Val β-CH$_3$'s), 1.18 (d, 3H, Ala β-CH$_3$), 1.50 (m, 2H, pentamide 4-CH$_2$), 1.95 (m, 1H, Val β-CH), 2.72 (t, 2H, CONHCH$_2$—CH$_2$Ph), 3.28 (m, 2H, CONHCH$_2$—CH$_2$Ph), 3.48 (m, 2H, pentamide 5-CH$_2$—OH), 3.87 (m, 2H, Ala, Val α—CH), 4.12 (m, 1H, pentamide 3-CH), 4,32 (m, 1H, pentamide 2-CH, 5.01 (s, 2H, Ph—CH$_2$—OCO), 5.74 (d, 1H, pentamide 2-CH-OH), 7.25 (m, 11H, aromatic H, CONH), 7.62 (t, 1H, CONH), 7.82 (t, 1H, CONH), 7.93 (d, 1H, CONH); FABMS (calculated for C$_{35}$H$_{55}$N$_4$O$_7$Si, 671.3840) m/e 671.3895 (M$^+$+1).

N-(3-Phenylpropyl)-3-(N-benzyloxycarbonylvalylalanylamino) -5-t-butyldimethylsilyloxy-2-hydroxypentamide (53). This was prepared in a manner identical to that for 50, except using 1.00 g (1.7 mmol) of 49 to give 1.01 g (1.4 mmol, 84%) of a solid (enatiomeric ratio was not determined): R$_f$=0.42, 0.30 (EtOAc); $^1$H NMR (DMSO-d$_6$) δ–0.05 (s, 6H, Si—CH$_3$'s), 0.81 (m, 15H, Si—t—Bu, Val β-CH$_3$'s), 1.17 (d, 3H, Ala β-CH$_3$), 1.57 (m, 2H, pentamide 4-CH$_2$), 1.70 (m, 2H, CONHCH$_2$—CH$_2$—CH$_2$Ph), 1.95 (m, 1H, Val β-CH), 2.53 (t, 2H, CONHCH$_2$—CH$_2$—CH$_2$Ph), 3.10 (m, 2H, CONHCH$_2$—CH$_2$—CH$_2$Ph), 3.51 (m, 2H, pentamide 5-CH$_2$—OH), 3.87 (m, 2H, Ala, Val α-CH), 4.12 (m, 1H, pentamide 3-CH), 4,32 (m, 1H, pentamide 2-CH), 5.01 (s, 2H, Ph—CH$_2$—OCO), 5.73 (d, IH, pentamide 2-CH-OH), 7.25 (m, 11H, aromatic H, CONH), 7.65 (d, 1H, CONH), 7.80 (t, 1H, CONH), 7.93 (d, 1H, CONH); FABMS (calculated for C$_{36}$H$_{57}$N$_4$O$_7$Si, 685.0) m/e 685.3 (M$^+$+1).

General Procedure for Compounds 54–57 (Cbz—Ala—Asp—CONH—CH$_2$CH$_2$Ph, 54). Upon stirring a solution of 50 (1.10 g, 1.9 mmol) in CH$_2$Cl$_2$ (6 mL) and Et$_2$O (2 mL) with cooling (ice bath), chromiium trioxide (0.38 g, 3.8 mmol) was added and the mixture was stirred at 5° C. under an argon atmosphere for 2 hours. The solvent was removed from the mixture under reduced pressure. Acetic acid (7 mL), H$_2$O (0.8 mL), and CrO$_3$ (0.77 g, 7.6 mmol) were added and the mixture was stirred at room temperature for 3 hours. The resulting mixture was diluted with EtOAc/isopropanol (10:1, 100 mL), dried over MgSO$_4$, and filtered through silica gel. The solvent was removed from the filtrate and the crude product was purified by gel column chromatography (EtOAc) to give 0.16 g (0.34 mmol, 17% yield) of a colorless oil ($R_f$=0.54, EtOAc).

TABLE III

Physical properties of α-Keto Amides.

| no. | mp (° C.) | Formula | FABMS m/e ($M^+$ + 1) Calculated | FABMS m/e ($M^+$ + 1) Found | Anal. |
|---|---|---|---|---|---|
| 12 | 65–67 | $C_{18}H_{24}N_2O_6$ | 365.1713 | 365.1738 | C, H, N |
| 13 | 116–117 | $C_{19}H_{26}N_2O_6$ | 379.1869 | 379.1860 | C, H, N |
| 14 | 135–137 | $C_{19}H_{20}N_2O_6$ | 373.1399 | 373.1368 | C, H, N |
| 15 | 128–129 | $C_{21}H_{22}N_2O_6$ | 399.1556 | 399.1579 | C, H, N |
| 24 | nd | $C_{13}H_{17}N_2O_4Cl$ | 265.1188 | 265.1178* | C, H, N |
| 25 | nd | $C_{14}H_{19}N_2O_4Cl$ | 279.1345 | 279.1372* | C, H, N |
| 26 | 181–182 | $C_{20}H_{22}N_2O_6S$ | 419.1277 | 419.1263 | C, H, N |
| 27 | 120–121 | $C_{20}H_{27}N_3O_6$ | 406.1978 | 406.1993 | C, H, N |
| 28 | 147–149 | $C_{28}H_{34}N_4O_7$ | 539.2506 | 539.2487 | C, H, N |
| 29 | 160–162 | $C_{29}H_{36}N_4O_7$ | 553.2662 | 553.2659 | C, H, N |
| 31 | 215–216 | $C_{30}H_{38}N_4O_7$ | 567.2819 | 567.2845 | C, H, N |
| 33 | 198–199 | $C_{30}H_{37}N_4O_7Cl$ | 601.2429 | 601.2465 | C, H, N |
| 35 | 140–142 | $C_{32}H_{41}N_5O_9$ | 640.2982 | 640.2963 | C, H, N |
| 36 | 161–163 | $C_{33}H_{43}N_5O_9$ | 654.3139 | 654.3110 | C, H, N |
| 54 | nd | $C_{24}H_{27}N_3O_7$ | 470.1927 | 479.1936 | C, H, N |
| 55 | nd | $C_{25}H_{29}N_3O_7$ | 484.2084 | 484.2154 | C, H, N |
| 56 | 135–137 | $C_{29}H_{36}N_4O_8$ | 569.2611 | 569.2634 | C, H, N |
| 57 | nd | $C_{30}H_{38}N_4O_8$ | 583.2768 | 583.2781 | C, H, N |

*$[M + H—HCl]^+$

TABLE IV

Proton NMR Data (DMSO-d6) for Selected Compounds.

| no. | major signals |
|---|---|
| 12 | 1.42(s, 9H, Boc $CH_3$'s), 2.74(t, 2H, $CH_2$Ph), 2.95(obs, 2H, β-$CH_2$), 3.30 (m, 2H, NH$CH_2$), 4.82(m, 1H, α-CH), 7.24(m, 5H, aromatic CH's), 8.65(br, 1H, COOH). |
| 13 | 1.38(s, 9H, Boc $CH_3$'s), 1.67(t, 2H, $CH_2CH_2CH_2$Ph), 2.57(obs, 2H, $CH_2$Ph), 2.61(m, 1H, 1 of β-$CH_2$), 3.11(m, 3H, NH$CH_2$ & 1 of β-$CH_2$), 4.26 (m, 1H, α-CH), 7.01(d, 1H, urethane NH), 7.21(m, 5H, aromatic CH's), 7.85 (br, 1H, amide NH), 8.80(br, 1H, COOH). |
| 15 | 2.68(m, 4H, β-$CH_2$, $CH_2CH_2$Ph), 3.31(m, 2H, CONH$CH_2CH_2$), 5.01(m, 3H, α-$CH_2$, Ph$CH_2$OCO), 7.25(m, 10H, aromatic H), 7.75(d, 1H, OCONH), 8.78(t, 1H, keto amide NH), 12.46(br, 1H, COOH). |
| 24 | 2.73(t, 2H, $CH_2$Ph), 3.37(m, 4H NH$CH_2$ & β-$CH_2$), 3.97(m, 1H, α-CH), 7.24(m, 5H, aromatic CH's), 8.61(br, 3H, $NH_3^+$), 8.75(t, 1H, amide NH). |
| 25 | 1.72(m, 2H, $CH_2CH_2CH_2$Ph), 2.58(t, 2H, $CH_2$Ph), 2.80(ABX, 2H, β-$CH_2$), 3.09(m, 2H, NH$CH_2$), 4.00(m, 1H, α-CH), 7.22(m, 5H, aromatic CH's), 8.57 (br, 3H, $NH_3^+$), 8.79(br, 1H, amide NH). |
| 26 | 2.67(m, 4H, $CH_2$Ph & β-$CH_2$), 3.25(q, 2H, NH$CH_2$), 4.60(q, 1H, α-CH), 5.08(s, 2H, benzyl $CH_2$), 7.31(m, 10H, aromatic CH's), 7.97(br, 1H, amide NH), 8.17(d, 1H, sulfonamide NH), 8.75(br, 1H, COOH). |
| 27 | 0.84(d, 6H,$(CH_3)_2$CH$CH_2$CO), 1.93(m, 3H, $(CH_3)_2C$H$CH_2$CO, Ph$CH_2CH_2$NHCO), 2.73(m, 4H, Asp β-$CH_2$, Ph$CH_2CH_2$NHCO), 3.15(d, 2H,$(CH_3)_2$CH$CH_2$CO, 3.69(d, 2H, Gly α-$CH_2$), 5.06(br, 1H, Asp α-CH), 7.20(m, aromatic CH's), 7.99(t, 1H, $(CH_3)_2$CHCH$_2$CON$H$), 8.22(br, 1H, Gly amide NH), 8.66(br, 1H, α-keto amide NH). |
| 28 | 1.14(m, 6H, 2 Ala $CH_3$'s), 2.44(m, 6H, Ph$CH_2$CH$_2$CO, Ph$CH_2$CH$_2$NHCO, Asp β-$CH_2$'s), 3.27(m, 5H, Ph$CH_2$CH$_2$CO, Ph$CH_2CH_2$NHCO, COOH), 4.26 (m, 2H, Ala α-CH), 5.00(br, 1H, Asp α-CH), 7.20(m, 10H, aromatic CH's), 8.03(m, 3H, Ala, Asp amide NH's), 8.63(br, 1H, α-keto amide NH). |
| 29 | 0.80(m, 6H, Val $CH_3$'s), 1.91(m, 1H, Val β-CH), 2.40(m, 4H, Ph$CH_2$CH$_2$CONH, COCONHCH$_2CH_2$Ph), 2.77(m, 6H, Asp β-$CH_2$'s, Ph$CH_2CH_2$CONH, COCONH$CH_2$CH$_2$Ph), 3.72(m, 2H, Gly α-$CH_2$), 4.09 (m, 1H, Val α-CH), 5.15(br, 1H, Asp α-CH), 7.21(m, aromatic CH's), 7.93 (m, 3H, Val, Gly, Asp amide NH), 8.71(br, 1H, α-keto amide NH), 12.38(br, 1H, COOH). |
| 31 | 0.75(m, 6H, Val $CH_3$'s), 1.16(m, 3H, Ala $CH_3$), 1.91(m, 1H, Val β-CH), 2.45(m, 4H, Asp β-$CH_2$'s, Ph$CH_2CH_2$CO), 2.76(m, 6H, Ph$CH_2CH_2$NHCO, Ph$CH_2$CH$_2$CO), 4.14(t, 1H, Val α-CH), 4.28(t, 1H, Ala α-CH), 5.03,(br, 1H, Asp α-CH), 7.20(m, 10H, aromatic CH's), 7.85(d, 1H, Val amide NH), 8.00 (d, 1H, Ala amide NH), 8.26(br, 1H, Asp amide NH), 8.68(br, 1H, α-keto amide NH), 12.42(br, 1H, COOH). |
| 33 | 0.74(m, 6H, Val $CH_3$'s), 1.16(m, 3H, Ala $CH_3$), 1.89(m, 1H, Val β-CH), 2.43(m, 4H, Asp β-$CH_2$+s, PhCH$_2CH_2$CO), 2.72(m, 6H, Ph$CH_2CH_2$NHCO, Ph$CH_2$CH$_2$CO), 4.13(t, 1H, Val α-CH), 4.28(t, 1H, Ala α-CH), 5.04,(br, 1H, |

TABLE IV-continued

Proton NMR Data (DMSO-d6) for Selected Compounds.

| no. | major signals |
|---|---|
|  | Asp α-CH), 7.20,(m, 9H, aromatic CH's), 7.86(d, 1H, Val amide NH), 8.00(d, 1H, Ala amide NH), 8.26(br, 1H, Asp amide NH), 8.69(br, 1H, α-keto amide NH), 12.48(br, 1H, COOH). |
| 35 | 0.76(m, 6H, Val $CH_3$'s), 1.19(d, 3H, Ala $CH_3$), 1.75(s, 3H, Ac $CH_3$), 1.94 (m, 1H, Val β-CH), 2.68(m, 6H, $CH_2$Ph, Asp & Tyr β-$CH_2$'s), 3.26(q, 2H, NH<u>CH</u>$_2$EE), 4.19 & 4.48(m, 4H, α-CH's), 6.62 & 7.02(2 × d, 4H, Tyr aromatic CH's), 7.21(m, 5H, phenyl aromatic CH's), 7.75(t, 1H, amide NH), 7.84(d, 1H, amide NH), 7.92(d, 1H, amide NH), 8.07(m, 2H, amide NH's), 9.15(br, 1H, Tyr OH). |
| 36 | 0.77(2 × d, 6H, Val $CH_3$'s), 1.21(d, 3H, Ala $CH_3$), 1.66(m, 2H, $CH_2$<u>CH</u>$_2$$CH_2$Ph), 1.75(s, 3H, Ac $CH_3$), 1.95(m, 1H, Val β-CH), 2.70(m, 6H, $CH_2$Ph, Asp & Tyr β-$CH_2$+s), 3.05(app q, 2H, NH<u>CH</u>$_2$), 4.20 & 4.48(m, 4H, α-CH's), 6.63 & 7.02(2 × d, 4H, Tyr aromatic CH's), 7.25(m, 5H, phenyl aromatic CH's), 7.83 & 8.08(m, 5H, amide NH's), 9.18(br, 1H, Tyr OH), 11.06(br, 1H, COOH). |
| 54 | 1.22(d, 3H, Ala $CH_3$), 2.75(t, 2H, C—<u>CH</u>$_2$—Ph), 2.99(t, 2H, Asp β-$CH_2$), 3.34 (m, 2H, CONH—<u>CH</u>$_2$—$CH_2$Ph), 4.32(m, 3H, Ala α-CH, PhCH$_2$OCON<u>H</u>, Asp α-CH), 5.00(s, 2H, Ph—<u>CH</u>$_2$—OCO), 7.28(m, 10H, aromatic H), 7.66(d, 1H, Asp amide NH), 8.99(t, 1H, keto amide N<u>H</u>), 10.89(s, 1H, COOH). |
| 55* | 1.38(d, 3H, Ala $CH_3$), 1.87(m, 2H, CONHCH$_2$—<u>CH</u>$_2$—$CH_2$Ph), 2.64(t, 2H, C—<u>CH</u>$_2$—Ph), 3.12(m, 2H, Asp β-$CH_2$), 3.33(m, 2H, CONH—<u>CH</u>$_2$—$CH_2$Ph), 4.52 (m, 3H, Ala α-CH, CONH, Asp α-CH), 5.09(dd, 2H, Ph—<u>CH</u>$_2$—OCO), 5.78(d, 1H, PHCH$_2$OCON<u>H</u>), 7.32(m, 11H, aromatic H, keto amide N<u>H</u>), 9.66(s, 1H, COOH). |
| 56* | 0.93(dd, 6H, Val $CH_3$'s), 1.36(d, 3H, Ala $CH_3$), 2.09(m, 1H, Val β-CH), 2.84(t, 2H, CONHCH$_2$—<u>CH</u>$_2$Ph), 3.15(m, 2H, Asp β-$CH_2$), 3.56(dd, 2H, CONHCH$_2$—<u>CH</u>$_2$Ph), 4.08(m, 1H, Ala α-CH), 4.51(m, 1H, Val α-CH), 4.70 (m, 1H, Asp α-CH), 5.11(s, 2H, PhC<u>H</u>$_2$OCO), 5.75(d, 1H, PhCH$_2$OCON<u>H</u>), 7.26(m, 13H, aromatic CH's, Ala, Asp, amide NH's, α-keto amide NH), 9.75 (s, 1H, COOH). |
| 57 | 0.84(dd, 6H, Val $CH_3$'s), 1.24(m, 3H, Ma $CH_3$), 1.74(p, 2H, CONHCH$_2$—<u>CH</u>$_2$—$CH_2$Ph), 1.94(m, 1H, Val β-CH), 2.55(t, 2H, CONHCH$_2$—$CH_2$—$CH_2$Ph), 2.99(t, 2H, CONH<u>CH</u>$_2$—$CH_2$—$CH_2$Ph), 3.12(dd, 2H, Asp β-$CH_2$), 3.88(m, 1H, Ala α-CH), 4.41(m, 3H, Asp α-CH, PhCH$_2$OCON<u>H</u>, Val α-CH), 5.01(s, 2H, PhCH$_2$-OCO), 7.28(m, 11H, aromatic CH's, Val amide NH), 8.24(d, 1H, Ala amide NH), 8.96(t, 1H, α-keto amide NH), 10.85(br, 1H, COOH). |

*Data obtained in $CDCl_3$.

It is obvious that those skilled in the art may make modifications to the invention without departing from the spirit of the invention or the scope of the subjoined claims and their equivalents.

What is claimed is:

1. A compound of the formula:

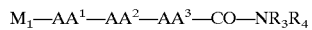

or a pharmaceutically acceptable salt, wherein $M_1$ represents H, $NH_2$—CO—, $NH_2$—CS—, $NH_2$—$SO_2$—, X—NH—CO—, $X_2$N—CO—, X—NH—CS—, $X_2$N—CS—, X—NH—$SO_2$—, $X_2$N—$SO_2$—, X—CO—, X—CS—, X—$SO_2$—, X—O—CO, X—O—CS—;

X is selected from the group consisting of $C_{1-10}$ alkyl, $C_{1-10}$ fluoroalkyl, $C_{1-10}$ alkyl substituted with J, $C_{1-10}$ fluoroalkyl substituted with J, 1-admantyl, 9-fluorenyl, phenyl, phenyl substituted with K, phenyl disubstituted with K, phenyl tisubstituted with K, naphthyl, naphthyl substituted with K, naphthyl disubstituted with K, naphthyl trisubstituted with K, $C_{1-10}$ alkyl with an attached phenyl group substituted with K, $C_{1-10}$ alkyl with two attached phenyl groups substituted with K, $C_{1-10}$ alkyl with an attached phenoxy group, and $C_{1-10}$ alkyl with an attached phenoxy group substituted with K on the phenoxy group;

J is selected from the group consisting of halogen, COOH, OH, CN, $NO_2$, $NH_2$, $C_{1-10}$ alkoxy, $C_{1-10}$ alkylamine, $C_{2-12}$ dialkylamine, $C_{1-10}$ akyl—O—CO—, $C_{1-10}$ alkyl—O—CO—NH—, and $C_{1-10}$ alkyl—S—;

K is selected from the group consisting of halogen, $C_{1-10}$ alkyl, $C_{1-10}$ perfluoroalkyl, $C_{1-10}$ alkoxy, $NO_2$, CN, OH, $CO_2$H, amino, $C_{1-10}$ alkylamino, $C_{2-12}$ dialkylamino, $C_{1-10}$ acyl, and $C_{1-10}$ alkoxy—CO—, and $C_{1-10}$ alkyl—S—;

$AA^1$ and $AA^2$ are the same or different and are side chain blocked or unblocked amino acids with the L configuration, D configuration, or no chirality at the a-carbon selected from the group consisting of alanine, valine, leucine, isoleucine, glycine, serine, aspartic acid, and glutamic acid;

$AA^3$ is selected from the group consisting of aspartic acid and glutamic acid;

$R_3$ is selected from the group consisting of $C_{2-3}$ alkyl with a phenyl group attached to the $C_{2-3}$ alkyl, $C_{3-20}$ cyclized alkyl with an attached phenyl group, $C_{1-20}$ alkyl with an attached phenyl group substituted with K, $C_{1-20}$ alkyl with an attached phenyl group disubstituted with K, $C_{1-20}$ alkyl with an attached phenyl group trisubstituted with K, $C_{3-20}$ cyclized alkyl with an attached phenyl group substituted with K, —NH—$CH_2CH_2$—(4-hydroxyphenyl), and —NH—$CH_2CH_2$—(3-indolyl); and $R_4$ is selected from the group consisting of H, $C_{3-20}$ alkyl, cyclized alkyl, $C_{1-20}$ alkyl with a phenyl group attached to the $C_{1-20}$ alkyl, $C_{3-20}$ cyclized alkyl with an attached phenyl group, $C_{1-20}$ alkyl with an attached phenyl group substituted with K, $C_{1-20}$ alkyl with an attached phenyl group disubstituted with K, $C_{1-20}$ alkyl with an attached phenyl group trisubstituted with K, $C_{3-20}$ cyclized alkyl with an attached phenyl group substituted with K, —NH—CH$_2$CH$_2$—(4-hydroxyphenyl), and —NH—CH$_2$CH$_2$—(3-indolyl).

2. A compound according to claim 1, or a pharmaceutically acceptable salt thereof, wherein $M_1$ is selected from the group consisting of X—CO and X—O—CO, and $R_4$ is H.

3. A compound according to claim 2, or a pharmaceutically acceptable salt thereof, wherein X is selected from the group consisting of $C_{1-10}$ alkyl, phenyl, phenyl substituted with K, $C_{1-10}$ alkyl with an attached phenyl group, $C_{1-10}$ alkyl with an attached phenyl group substituted with K, and $R_3$ is selected from the group consisting of $C_{1-20}$ alkyl with a phenyl group attached to the $C_{1-20}$ alkyl.

4. A compound of the formula:

or a pharmaceutically acceptable salt, wherein $M_1$ represents H, NH$_2$—CO—, NH$_2$—CS—, NH$_2$—SO$_2$—, X—NH—CO—, X$_2$N—CO—, X—NH—CS—, X$_2$N—CS—, X—NH—SO$_2$—, X$_2$N—SO$_2$—, X—CO—, X—CS—, X—SO$_2$—, X—O—CO, X—O—CS—;

X is selected from the group consisting of $C_{1-10}$ alkyl, $C_{1-10}$ fluoroalkyl, $C_{1-10}$ alkyl substituted with J, $C_{1-10}$ fluoroalkyl substituted with J, 1-admantyl, 9-fluorenyl, phenyl phenyl substituted with K, phenyl disubstituted with K, phenyl trisubstituted with K, naphthyl, naphthyl substituted with K, naphthyl disubstituted with K, naphthyl trisubstituted with K, $C_{1-10}$ alkyl with an attached phenyl group substituted with K, $C_{1-10}$ alkyl with two attached phenyl groups substituted with K, $C_{1-10}$ alkyl with an attached phenoxy group, and $C_{1-10}$ alkyl with an attached phenoxy group substituted with K on the phenoxy group;

J is selected from the group consisting of halogen, COOH, OH, CN, NO$_2$, NH$_2$, $C_{1-10}$ alkoxy, $C_{1-10}$ alkylamine, $C_{2-12}$ dialkylamine, $C_{1-10}$ alkyl-O—CO—, $C_{1-10}$ alkyl—O—CO—NH—, and $C_{1-10}$ alkyl—S—;

K is selected from the group consisting of halogen, $C_{1-10}$ alkyl, $C_{1-10}$ perfluoroalkyl, $C_{1-10}$ alkoxy, NO$_2$, CN, OH, CO$_2$H, amino, $C_{1-10}$ alkylamino, $C_{2-12}$ dialkylamino, $C_{1-10}$ acyl, and $C_{1-10}$ alkoxy—CO—, and $C_{1-10}$ alkyl—S—;

$AA^1$ and $AA^2$ are the same or different and are side chain blocked or unblocked amino acids with the L configuration, D configuration, or no chirality at the a-carbon selected from the group consisting of alanine, valine and glycine;

$AA^3$ is selected from the group consisting of aspartic acid and glutamic acid;

$R_3$ is selected from the group consisting of $C_{2-3}$ alkyl with a phenyl group attached to the $C_{2-3}$ alkyl, $C_{3-20}$ cyclized alkyl with an attached phenyl group, $C_{1-20}$ alkyl with an attached phenyl group substituted with K, $C_{1-20}$ alkyl with an attached phenyl group disubstituted with K, $C_{1-20}$ alkyl with an attached phenyl group trisubstituted with K, $C_{3-20}$ cyclized alkyl with an attached phenyl group substituted with K, —NH—CH$_2$CH$_2$—(4-hydroxyphenyl), and —NH—CH$_2$CH$_2$—(3-indolyl); and $R_4$ is selected from the group consisting of H, $C_{1-20}$ alkyl, $C_{3-20}$ cyclized alkyl, $C_{1-20}$ alkyl with a phenyl group attached to the $C_{1-20}$ alkyl, $C_{3-20}$ cyclized alkyl with an attached phenyl group, $C_{1-20}$ alkyl with an attached phenyl group substituted with K, $C_{1-20}$ alkyl with an attached phenyl group disubstituted with K, $C_{1-20}$ alkyl with an attached phenyl group trisubstituted with K, $C_{3-20}$ cyclized alkyl with an attached phenyl group substituted with K, —NH—CH$_2$CH$_2$—(4-hydroxyphenyl), and —NH—CH$_2$CH$_2$—(3-indolyl).

5. A compound according to claim 1, or a pharmaceutically acceptable salt thereof, wherein $M_1$ is selected from the group consisting of X—CO and X—O—CO, and $R_4$ is H.

6. A compound according to claim 5, a pharmaceutically acceptable salt thereof, wherein X is selected from the group consisting of $C_{1-10}$ alkyl, phenyl, phenyl substituted with K, $C_{1-10}$ alkyl with an attached phenyl group, $C_{1-10}$ alkyl with an attached phenyl group substituted with K, and $R_3$ is selected from the group consisting of $C_{1-20}$ alkyl with a phenyl group attached to the $C_{1-20}$ alkyl.

* * * * *